(12) United States Patent
Rickards et al.

(10) Patent No.: US 6,632,822 B1
(45) Date of Patent: Oct. 14, 2003

(54) COMPOUNDS AND THERAPEUTIC METHODS

(75) Inventors: Rodney W. Rickards, Weetangera (AU); Geoffrey D. Smith, Lyneham (AU); Kiaran Kirk, O'Connor (AU)

(73) Assignee: The Australian National University, Acton (AU)

( * ) Notice: Subject to any disclaimer, the term of this patent is extended or adjusted under 35 U.S.C. 154(b) by 0 days.

(21) Appl. No.: 09/980,506

(22) PCT Filed: May 12, 2000

(86) PCT No.: PCT/AU00/00458

§ 371 (c)(1),
(2), (4) Date: Feb. 27, 2002

(87) PCT Pub. No.: WO00/69856

PCT Pub. Date: Nov. 23, 2000

(30) Foreign Application Priority Data

May 21, 1999 (AU) ............................................. PQ 0506
May 14, 1999 (AU) ............................................. PQ 0373

(51) Int. Cl.[7] ...................... A61K 31/47; C07D 471/02
(52) U.S. Cl. ............................ 514/280; 546/49; 546/56
(58) Field of Search ............................. 514/280; 546/49, 546/56

(56) References Cited

U.S. PATENT DOCUMENTS 6,204,292 B1    3/2001   Kozikowski et al. ......... 514/561
6,362,196 B1    3/2002   Kulagowski ................. 514/307

OTHER PUBLICATIONS

Mohanakrishanan, A.K. et al.: A versatile construction of the 8H–quino[4,3–b]carbazole ring system as a potential DNA binder. J. Org. Chem. vol. 60, pp. 1939–1946, 1995.*
Rickards, R.W. et al.: Calothrixins A and B, novel pentacyclic metabolites from Calothrix Cyanobacteria with potent activity against malaria parasites and human cancer cells. Teatrahedron, vol. 55, pp. 13513–13520, 1999.*

*A Dictionary of Genetics*, 4th Edition, Robert C. King & William D. Stansfield, Oxford University Press, 1990, pp 141.
*Concise Encyclopedia Chemistry*, Translated and Revised by Mary Eagleson, Walter DeGruyter Bevlin, New York, 1994, pp 895.
*Hawley's Condensed Chemical Dictionary*, 1987, pp. 967.
*Remington's Pharmaceutical Sciences*, 18th Ed., Mack Publishing Company, 1990, pp 1686.
*The Dictionary of Cell & Molecular Biology* JM Lackie & JAT Dow, 3rd Ed. Academic Press, 1999, pp. 209.
Mohanakrishnan, A.K., et al., "A Versatile Construction of the 8H–Quino[4,3–b]carbazole Ring System as a Potential DNA Binder", *Journal of Organic Chemistry*, vol. 60, (1995) No. 7, pp 1939–1946.
Rickards, R., et al., "Calothrixins A and B, Novel Pentacyclic Metabolites from Calothrix Cyanobacteria with Potent Activity against Malaria Parasites and Human Cancer Cells", Tetrahedron 55 (1999) 13513–13520.
Schlegel, I., et al., "Antibodic activity of new cyanobacterial isolates from Australia and Asia against green algae and cyanobacteria" *Journal of Applied Phycology*, (1999), 10:471–479.
Takara, K. et al., "Cytotoxic Effects of 27 Anticancer Drugs in HeLa and MDRI–Overexpressing Derivative Cell Lines," *Biol. Pharm Bull*. 25(6), Jun. 2002, pp 771–778.
Elango S., et al., "Synthesis of Quinolono [4,3–b] and [3,4–b] Carbazoles Potential DNA Binders" *Tetrahedron Letters*, vol. 34, No. 8, 1993, pp 1347–1350.
Ziegler, C.J., et al., "High–throughput synthesis and screening of platinum drug candidates" *J. Biol Inorg. Chem*., Oct. 2000 5:774–783.

* cited by examiner

Primary Examiner—Charanjit S. Aulakh
(74) Attorney, Agent, or Firm—Greenlee, Winner and Sullivan, P.C.

(57) ABSTRACT

The present invention relates to indolo[3,2-j]phenanthridine compounds and their use in the treatment of cancer and other diseases of humans and animals including parasitic diseases such as those of Apicomplexan origin, compositions containing said compounds and methods of treatment using them.

14 Claims, 6 Drawing Sheets

Figure 1

COMPOUNDS AND THERAPEUTIC METHODS

CROSS-REFERENCE TO RELATED APPLICATIONS

This application takes priority from PCT Application PCT/AU00/00458, filed May 12, 2000, which takes priority from Australian Patent Application PQ0373/99, filed May 14, 1999 and Australian Patent Application PQ0506/99, filed May 21, 1999.

TECHNICAL FIELD

The present invention relates generally to compounds containing a indolo[3,2-j]phenanthridine ring system. In particular, the present invention relates to compounds which are useful in the treatment of cancer and other diseases of humans and animals, particularly parasitic diseases, such as those of apicomplexan origin, compositions containing said compounds and methods of treatment using them.

BACKGROUND ART

Despite the significant advances made by the medical and scientific community over the last fifty years, a number of potentially mortal and debilitating mammalian, particularly humanp diseases are yet to be conquered by effective and adequate prophylaxis, treatment or cure. Two examples of such diseases are cancer and malaria.

Malaria is a disease which has been estimated to affect approximately 5% of the World's population at any time, accounts for 25–50% of all hospital admissions in Africa, and is responsible for the death of between 1 to 2 million children each year.

The disease is caused by the entry of an apicomplexan parasite, Plasmodium, particularly *P. falciparum* or *P. vivax* into the bloodstream, through the bites of females of certain mosquito species which transmit the disease from one host to another. The parasite invades the liver and the red blood cells of the host and manifests its presence in the well recognised symptoms of chills, shivering, fever and profuse sweating. If left untreated, the disease chronically manifests itself through regularly recurring bouts of fever and prostration. Repeated attacks may result in the development of anaemia and enlargement of the liver and spleen. In the very young or old, the disease can be fatal.

Chloroquine has become the standard antimalarial for the treatment and prophylaxis of human malarial diseases and has become one of the most widely used drugs in the world. Increasingly, however, the parasites have developed resistance to the drug and *P. falciparum* is now almost untreatable with chloroquine and many strains of *P. vivax* are also resistant. Although quinine is often used against chloroquinine resistant strains of Plasmodium it is poorly tolerated and compliance is low. (White, N. J. (1992), *J. Antimicrob. Chemother.* 30, 571–85; Krishna, S. (1997), *Br. Med. J.*, 315, 730–32). Other drugs such as mefloquine produce undesirable side effects.

Accordingly, there exists a need for new anti-malarial drugs which are effective against Plasmodium.

Another disease which has long been the subject of intense research by the medical and scientific communities is cancer. The growth, development and death of normal cells are highly regulated by mechanisms which are not yet fully understood. When these regulatory controls cease or malfunction, due to either external or genetic factors, the aberrant cells multiply at a greater rate than normal. Malignant tumours can metastasise throughout the body and invade other tissues and organs. The aetiology of cancer remains incompletely understood and despite advances in the detection and treatment of cancerous conditions over the last several decades, there remains a continued need for the development of new anticancer agents.

DISCLOSURE OF THE INVENTION

The present inventors have now isolated for the first time, specific compounds from extracts of certain Calothrix strains of cyanobacteria which have bioactivity against Plasmodium and cancer cells and may provide new treatments for mammalian diseases, including parasitic diseases such as malaria, or cancerous conditions. Without intending to limit the invention in any way, it has also been found that one mode of biochemical action of these compounds involves inhibition of DNA transcription or replication, and therefore, the present invention may also provide therapeutic and/or prophylactic methods for other conditions or infections.

Accordingly, in a first aspect, the present invention provides compounds of Formula (I):

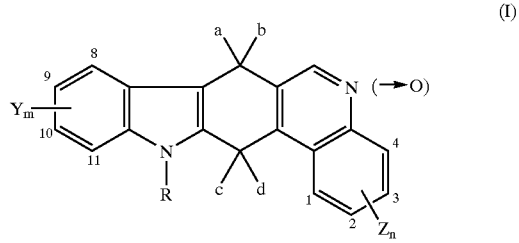

wherein

R is selected from hydrogen, alkyl, acyl, carboxyalkyl, carboalkoxyalkyl;

m and n are independently selected from 0, 1, 2;

each Y and each Z are independently selected from halo, acyl, nitro, amino, alkylamino, acylamino, hydroxy, acyloxy, alkoxy, alkyl, $CO_2H$, $CO_2$alkyl, $CONX_2$ (where each X is independently H or alkyl), $SO_3H$, $SO_2NX_2$ (wherein each X is independently H or alkyl), nitrile, formyl, carboxyalkyl, carboalkoxyalkyl;

a, b, c and d are independently selected from hydrogen, hydroxy, alkoxy, acyloxy, alkyl; or, a and b together and/or c and d together independently form a carbonyl group (C=O), an imine group (C=N—$R^1$, where $R^1$ is alkyl, hydroxy, alkoxy or amino $NR^2R^3$), or an alkene group (C=$CR^2 R^3$, where $R^2$ and $R^3$ are independently hydrogen or alkyl);

or salt, derivative or prodrug thereof.

Compounds of Formula I can exist in their N-oxide form or as the free (unoxidized) base.

As used herein, the term "alkyl" denotes a straight, branched or cyclic fully saturated hydrocarbon residue of 1–6 carbon atoms including methyl, ethyl, n-propyl, iso-propyl, n-butyl, sec-butyl, t-butyl, n-pentyl, iso-pentyl, 2,2-dimethylpropyl, n-hexyl, 2-methylpentyl, 2,2-dimethylbutyl, 3-methylpentyl, 2,3-dimethylbutyl, cyclopropyl, cyclobutyl, cyclopentyl or cyclohexyl. Particularly preferred alkyl are methyl, ethyl, n- and iso-propyl, n-, sec and t- butyl. Optionally the alkyl group may be substituted by one or more halo, hydroxy, phenyl, amino, alkoxy, acyl, nitro, carboxylic acid, or carboxylic ester groups, for example halomethyl groups (eg $CF_3$, $CBr_3$) hydroxy alkyl groups (eg hydroxymethyl, hydroxyethyl), benzyl, aminoalkyl and alkoxyalkyl.

The term "acyl" is intended to refer to a group of the group of the formula —C(O)R', where R' is alkyl as defined above.

"Acyloxy" and "alkoxy" are taken to refer to acyl and alkyl groups when linked by an oxygen atom.

The term "halogen" denotes fluorine, chlorine, bromine or iodine.

Suitable alkoxy groups include methoxy, ethoxy, propoxy (n- and iso-) butoxy (n-, sec- and t-). Sitable carboxyalkyl groups include carboxymethyl, carboxyethyl, carboxybutyl, carboxypropyl. Suitable carboalkoxyalkyl include carbomethoxymethyl, carboethoxymethyl, carbopropoxymethyl, carbobutoxymethyl, carbomethoxyethyl, carboethoxyethyl, carbopropoxyethyl, carbobutoxyethyl, carbomethoxypropyl, carboethoxypropyl, carbopropoxypropyl, carbobutoxypropyl, carbomethoxybutyl, carboethoxybutyl, carbopropoxybutyl, carbobutoxybutyl. Suitable acyloxy include C(O)methyl, C(O)ethyl, C(O)propyl, C(O)butyl. Suitable $CO_2$alkyl includes $CO_2$methyl, $CO_2$ethyl, $CO_2$propyl, $CO_2$butyl. Suitable amides include $CONH_2$, CONHMe, CONHEt, CONHPr, $CONMe_2$, $CONEt_2$, $CONPr_2$. Suitable amino groups include $NH_2$, NHMe, NHEt, NHPr, $NMe_2$, $NEt_2$, $NPr_2$.

The term "salt, derivative or prodrug" refers to any pharmaceutically acceptable salt, ester, solvate, hydrate or any other compound which, upon administration to the recipient is capable of providing (directly or indirectly) a compound as described herein. However, it will be appreciated that non-pharmaceutically acceptable salts also fall within the scope of the invention since these may be useful in the preparation of pharmaceutically acceptable salts. The preparation of salts and prodrugs and derivatives can be carried out by methods known in the art.

Suitable pharmaceutically acceptable salts include salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others.

The compounds of the invention may be in crystalline form either as the free compounds or as solvates (e.g. hydrates) and it is intended that both forms are within the scope of the present invention. Methods of solvation are generally known within the art.

Any compound that is a prodrug of a compound of formula (I) is within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative.

It will be appreciated that some embodiments and derivatives of compounds of formula (I) may have an asymmetric centre, and therefore are capable of existing in more than one stereoisomeric form. The invention extends to each of these forms individually and to mixtures thereof, including racemates. The isomers may be separated conventionally by chromatographic methods or using a resolving agent.

In one embodiment, preferred compounds are where n and/or m are 0, 1 or 2, more preferably 0 or 1. In another embodiment, m and n are the same, ie both 0 or both 1 or both 2.

In another embodiment, preferred compounds are those where a and b together or c and d together form a carbonyl group. Particularly preferred embodiments are where a and b together and c and d together are both a carbonyl group.

Particularly preferred compounds are (IB) and its N-oxide (IA)

IA and IB

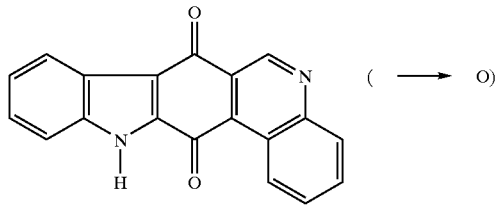

It will be appreciated that compounds of Formula (I) may be obtained by the application of common synthetic manipulations to the naturally derived IA and IB.

It will also be recognised that the quinoline moiety and its N-oxide are readily interconvertible by standard chemical methods and that one may be produced from the other or mixtures of the two.

It will also be understood that where R is alkyl or acyl, this may be achieved by standard N-alkylation or N-acylation of the indolo-nitrogen, to give, for example, >N-Me, >N-ethyl or >N—C(O)$CH_3$.

One or both of the quinonoid carbonyl groups may be subjected to reduction or nucleophilic addition manipulations such as those commonly employed in the art of organic synthetic chemistry. Thus, the reduction (for example with hydride reagents) of either of the carbonyl groups by one oxidation level affords >CH—OH; or, where the quinone itself is reduced by one oxidation level, the hydroquinol of the pentacyclic ring structure. Either or both of the resulting OH group(s) may be further alkylated or acylated using art known alkylating and acylating methodology to produce, for example >CH—OMe; >CH—OEt; >CH—OAc.

Further reduction of the aforementioned >CH—OH group can afford the unsubstituted central ring where the carbonyl group is replaced by the >$CH_2$ group.

Each of the carbonyl groups may also be independently subjected to nucleophilic addition conditions with suitable nucleophiles to form imines, oximes or alkenes. Thus, nucleophilic addition of a primary amine, $H_2N$—$R^1$(R= alkyl, preferably, methyl, ethyl or propyl), hydroxylamine, $H_2N$—OH, or a hydrazine $H_2NNR^1R^2$ ($R^1$ and $R^2$ are independently hydrogen or alkyl, preferably, methyl, ethyl or propyl) affords the imine, oxime or hydrazine respectively. Wittig reaction of the carbonyl group with a suitable phosphorous ylide offers access to the corresponding substituted alkene eg C=$CH_2$. Treatment of either or both of the carbonyl groups under suitable conditions with a Grignard reagent e.g MeMg BR or EtMgBr, replaces the carbonyl group with >C(OH)alkyl, eg >C(OH)Me or >C(OH)Et.

Alcoholysis of either or both of the carbonyl groups under appropriate conditions, offers access to acetals (>C(O alkyl)$_2$) eg. >C(O Me)$_2$ or >C(O Et)$_2$.

In one form, one of a and b, or c and d may be carbonyl while the other is an imine, oxime or alkene. In another form, both or a and b, and c and d may be imine or oxime or alkene. In another form of the invention at least one of a and b, or c and d, or both of a and b, and c and d, is >C(OH)alkyl or (>C(O alkyl)$_2$) where alkyl is preferably methyl, ethyl or propyl.

Where a, b, c and d are independently selected from hydrogen, hydroxy, alkoxy, acyloxy and alkyl, suitable aromatizing conditions may afford compounds where the central ring is aromatic and one of a or b and one of c or d have been eliminated. It will also be recognised that where hydroquinol is formed by suitable aromatizing conditions each aromatic OH group may be further alkylated or acylated. The quinol may also be formed by direct reduction of the quinone using known methods, for example catalytic reduction or by treatment with a hydride reagent, such as NaBH$_4$, or treatment with SnCl$_2$.

These fully aromatic compounds form another aspect of the invention.

Accordingly, in a second aspect, the invention also provides a compound of Formula II:

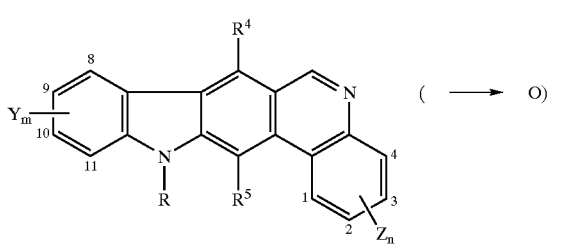

(II)

wherein

Y, Z, R, m and n are as herein described and

R$^4$ and R$^5$ are independently selected from hydrogen, hydroxy, alkoxy, acyloxy or alkyl;

or a salt, derivative or prodrug thereof.

Compounds of Formula (II) can exist in their N-oxide form or as the free (unoxidized) base.

Preferred R$^4$ and R$^5$ include hydrogen, hydroxy, methyl, ethyl, methoxy, ethoxy, propoxy, acetoxy.

In one preferred embodiment of Formula (II) at least one of R$^4$ or R$^5$ is hydroxy. In another preferred form, both R$^4$ and R$^5$ are hydroxy. One or both of the hydroxy groups may be further alkylated or acylated. In still another embodiment, one of R$^4$ or R$^5$ are hydrogen. In still a further embodiment of the invention R$^4$ and R$^5$ are both hydrogen.

Also contemplated as being within the scope of the present invention are compounds where one or both of the terminal aromatic 6-membered rings is further substituted. By employing commonly known aromatic substitution methodology one or both of the unsubstituted 6-membered aromatic rings may be further substituted by halo (preferably chloro, bromo or iodo), acyl, sulfonate, alkyl or nitro groups. The nitro group may be reduced (for example, by treatment with SnCl$_2$) to afford an aromatic amino group which may be further derivatized as described herein to afford alkylamino or acylamino groups. Alternatively, the aromatic nitro group may be converted into a hydroxy group, which may be further derivatised as described herein to afford alkoxy or acyloxy groups. Reduction of an aromatic acyl group under known conditions can provide an alkyl substituent. A sulfonic acid group (for example formed by treatment with fuming sulfuric acid) can be further converted ito sulfamides (SO$_2$NX$_2$). Alkyl groups can be oxidized to carboxylic acid groups (eg Me to CO$_2$H) using conventional oxidation procedures known in the art. Substituents at the same oxidation level (eg carboxyic acids, carboxylic esters, amides, nitrites) may be interconverted using methods known in the art. Reduction of groups such as carboxylic acids and carboxylic esters (eg using hydride reagents) can afford aldehydes and hydroxy groups.

Methods for aromatic substitution and conversion of the resulting substiuents are known in the art and are described in March, *Advanced Organic Chemistry* (3$^{rd}$. Edition), Wiley-Interscience and Larock, *Conmprehensive Organic Transformations,* 1989, VCH Publishers.

Preferred Y and Z include Cl, Br, I, OH, C(O)Me. C(O)Et, C(O)Pr, NH$_2$, NHMe, NHEt, NHPr, NMe$_2$, NEt$_2$, NPr$_2$, NHC(O)Me, OMe, OEt, OPr, CO$_2$H, CO$_2$Me, CO$_2$Et, CO$_2$Pr, CONH$_2$, SO$_3$H, SO$_2$NH$_2$, CHO, OC(O)Et, OC(O)CH$_3$.

Electrophilic aromatic substitution by a Y group may occur at the 8-, or 9-, or 10- or 11-position. Electrophilic aromatic substitution by a Z group may occur at the 1-, or 2-, or 3- or 4-position.

Acylation and alkylation of indolo- and amino-N atoms and free hydroxy groups may be carried out using any conventional procedure such as those generally known in the art or described or referenced in the Third Edition of March (supra). Examples of acylating agents suitable for the process of acylating the compounds of formulae (I) and (II) are carboxylic acids, acid halides and acid anhydrides. The reaction may be carried out in a conventional manner, for example in a solvent such as pyridine, dimethylformamide, etc., optionally in the presence of a coupling agent such as N,N'-dicyclohexylcarbodiimide, and optionally in the presence of a catalytic base such as 4-dimethylaminopyridine. The product of the reaction may be isolated in a conventional manner. Examples of alkylating agents suitable for the process of alkylating the compound of formula (I) are alkyl halides, such as methyl, ethyl, propyl, and benzyl chlorides, bromides and iodides; and dialkyl sulfates like dimethyl and diethyl sulfate.

It will be understood that in order to perform some of the synthetic manipulations, it may be necessary to selectively protect and/or deprotect reactive groups such as keto, carboxyl, ester, amide, hydroxy or amino groups. Suitable protecting groups and protection/deprotection methods are described in *Protective Groups in Organic Synthesis* by T W Greene and P. Wutz, John Wiley & Son, (1991) the contents of which are incorporated herein by reference. It is also to be understood that where synthetic manipulations provide a reactive group such as CO$_2$H, an ester, amide, an —OH or —NH$_2$ group, these may be further derivatized by suitable protecting groups. Such protected derivatives are also considered to be within the scope of the invention.

In another aspect, the invention relates to methods for making compounds of Formula I and (II), salts, derivative and prodrugs thereof as well as protected derivatives of same.

Compounds IA and IB (also referred to herein as calothrixins A and B respectively) were isolated from Calothrix strains (Schlegel et al, *J. Appl, Phycol.* 10, 471–479 (1998)), extracts of which were screened for activity against HeLa cells and Plasmodium as described in the Examples. Compound IA was screened against a chloroquine-resistant strain (FAF6, derived from ITG2 strain) of the malaria parasite *P.* falciparum and was shown to inhibit growth (FIG. 1). The $IC_{50}$ values of IA and chloroquine are presented in Table 1.

TABLE 1

| Compound | $IC_{50}$ (nM) |
|---|---|
| IA (Calothrixin A) | 58 ± 8 s.d. |
| IB (Calothrixin B) | 83 ± 17 s.d. |
| Chloroquine | 180 ± 44 s.d. |

Accordingly, in another aspect, the present invention provides a method for the prophylaxis or treatment of malarial diseases in a mammal comprising administering to said mammal a prophylactic or treatment effective amount of a compound according to Formula (I) or (II), or a pharmaceutically acceptable salt, derivative or prodrug thereof.

The present invention also provides for the use of a compound according to Formula (I) or (II), or a pharmaceutically acceptable salt, derivative or prodrug thereof, in the manufacture of a medicament for the prophylaxis or treatment of malarial diseases, as well as agents therefor comprising said compound.

The compounds of Formula IA and IB were also examined for their efficacy in inhibiting the growth of cultured HeLa cells (FIG. 2). The $IC_{50}$ values are depicted in Table 2.

TABLE 2

| Compound | $IC_{50}$ (nM) |
|---|---|
| IA (Calothrixin A) | 40 ± 9 s.d. |
| IB (Calothrixin B) | 350 ± 82 s.d. |

Accordingly, in yet another aspect, the present invention provides a method for the treatment of cancer in a mammal, comprising administering to said mammal a treatment effective amount of a compound according to Formula (I) or (II) or a pharmaceutically acceptable salt, derivative or prodrug thereof.

The invention also provides for the use of a compound of Formula (I) or (II), or a pharmaceutically acceptable salt, derivative or prodrug thereof, in the manufacture of a medicament for the treatment of cancer, as well as agents therefor comprising said compound.

In yet another aspect, the invention provides a method for the inhibition of DNA transcription in mammal, comprising administering to said mammal an inhibition effective amount of a compound according to Formula (I) or (II), or a pharmaceutically acceptable salt, derivative or prodrug thereof.

The invention also provides for the use of a compound of Formula (I) or (II) in the manufacture of a medicament for the inhibition of DNA transcription in a mammal.

The invention further relates to a method for the treatment or prophylaxis of a disease or condition in a mammal, wherein inhibition of DNA transcription is effective, comprising administering to said mammal an inhibition effective amount of a compound according to Formula (I) or (II), or a pharmaceutically acceptable salt, derivative or prodrug thereof.

Still another aspect of the invention relates to the use of a compound of Formula (I) or (II), or a pharmaceutically acceptable salt, derivative or prodrug thereof, in the manufacture of a medicament for the treatment or prophylaxis of a disease or condition wherein inhibition of DNA transcription is effective.

It will be recognised that where a and b, and c and/or are both hydroxy, these would be unstable compounds. Such compounds would not be suitable for use in the therapeutic methods of the invention.

The term "cancer" is used in its broadest sense and includes benign and malignant leukemias, sarcomas and carcinomas. The cancers contemplated by the present invention may be simple (monoclonal i.e. composed of a single neoplastic cell type), mixed (polyclonal, i.e. composed of more than one neoplastic cell type) or compound (i.e., composed of more than one neoplastic cell type and derived from more than one germ layer). Examples of simple cancers encompassed by the present invention include tumorous of mesenchymal origin (e.g. tumors of connective tissue, endothelial tissue, blood cells, muscle cells) and tumours of epithelial origin. Particular cancers contemplated by the present invention include, but are not limited to, fibrosarcoma, myxosarcoma, Ewing's sarcoma, granulocytic leukemia, basal cell carcinoma, colon cancer, gastric cancer, breast cancer, cancer of the uterus, ovarian cancer, lung cancer, prostate cancer, throat cancer, and a variety of skin cancers.

As used herein, the term "mammal" refers, to but is not limited to: humans, primates, livestock animals (e.g. sheep, cows, horses, goats, pigs), laboratory test animals (e.g. mice, rats, guinea pigs, rabbits) companion animals (e.g. cats, dogs), or captive wild animals. Preferred mammals are humans.

The term "treatment" is intended to include the slowing, interruption, arrest, reduction in the number of cancerous cells or eradication or cure of the disease or condition.

The term "effective amount" relates to an amount of compound which, when administered according to a desired dosing regimen, provides the desired prophylactic or therapeutic activity which desired activity may include the prevention, reduced severity, arresting or slowing the contraction or advancement of the condition. Dosing may occur as a single dosage or at intervals of minutes, hours, days, weeks, months or years or continuously over any one of these periods. Suitable dosages lie within the range of about 0.1 ng per kg of body weight to 1 g per kg of body weight per dosage. The dosage is preferably in the range of 1 $\mu$g to 1 g per kg of body weight per dosage. More preferably, the dosage is in the range of 1 mg to 1 g per kg of body weight per dosage. Suitably, the dosage is in the range of 1 $\mu$g to 500 $\mu$g per kg of body weight per dosage, such as 1 $\mu$g to 200 mg per kg of body weight per dosage, or 1 $\mu$g to 100 mg per kg of body weight per dosage. Other suitable dosages are in the range 1 mg to 250 mg per kg of body weight, including 1 mg to 10, 20, 50 or 100 mg per kg of body weight per dosage or 10 $\mu$g to 100 mg per kg of body weight per dosage.

The active ingredient may be administered in a single dose or a series of doses. When a compound of the invention is administered to a mammal, the dosage rate can normally be determined by the attending physician or veterinarian with the dosage generally varying according to the age, weight, and response of the patient as well as the severity of the subject's symptoms. While it is possible for the active ingredient to be administered alone, it is preferable to present it as a composition, preferably as a pharmaceutical composition.

Thus, in yet a further aspect, the invention also relates to compositions comprising a compound of Formula (I) or II or a salt derivative or prodrug thereof together with a pharmaceutically acceptable carrier, diluent or excipient.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent), preservative, disintegrant (e.g. sodium starch glycolate, cross-linked polyvinyl pyrrolidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions for rectal administration may be presented as a suppository with a suitable base comprising, for example, cocoa butter.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question; for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Where the mammal is non-human, the compounds according to the invention may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension;

(c) topical application, e.g. as a cream, ointment or spray applied to the skin; or (d) intravaginally, e.g. as a pessary, cream or foam.

In certain embodiments the present invention may also provide for compounds, agents, use, methods, or compositions which provide an advantage over (or avoid a disadvantage associated with) known compounds used in the chemotherapeutic prophylaxis or treatment of mammalian diseases such as malarial or cancerous conditions. Such advantages may include one or more of: increased therapeutic activity, reduced side effects, reduced cytoxicity to non-cancerous cells, improved physical characteristics for formulation into pharmaceutical compositions, greater patient compliance, improved stability or a more readily available means for obtaining said compound, e.g. simpler or higher yielding processes.

The compounds of the invention may also be useful in the treatment of other parasitic diseases such as those caused by worms, and spread by mosquitoes (eg African River virus).

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

MODES FOR CARRYING OUT THE INVENTION

The invention will now be illustrated by the following non-limiting Examples and Drawings. These are provided to assist in the further understanding of the invention, and the particular materials, conditions and compounds described are not to be construed as limiting the scope thereof.

BRIEF DESCRIPTION OF THE DRAWINGS

Figure 1:
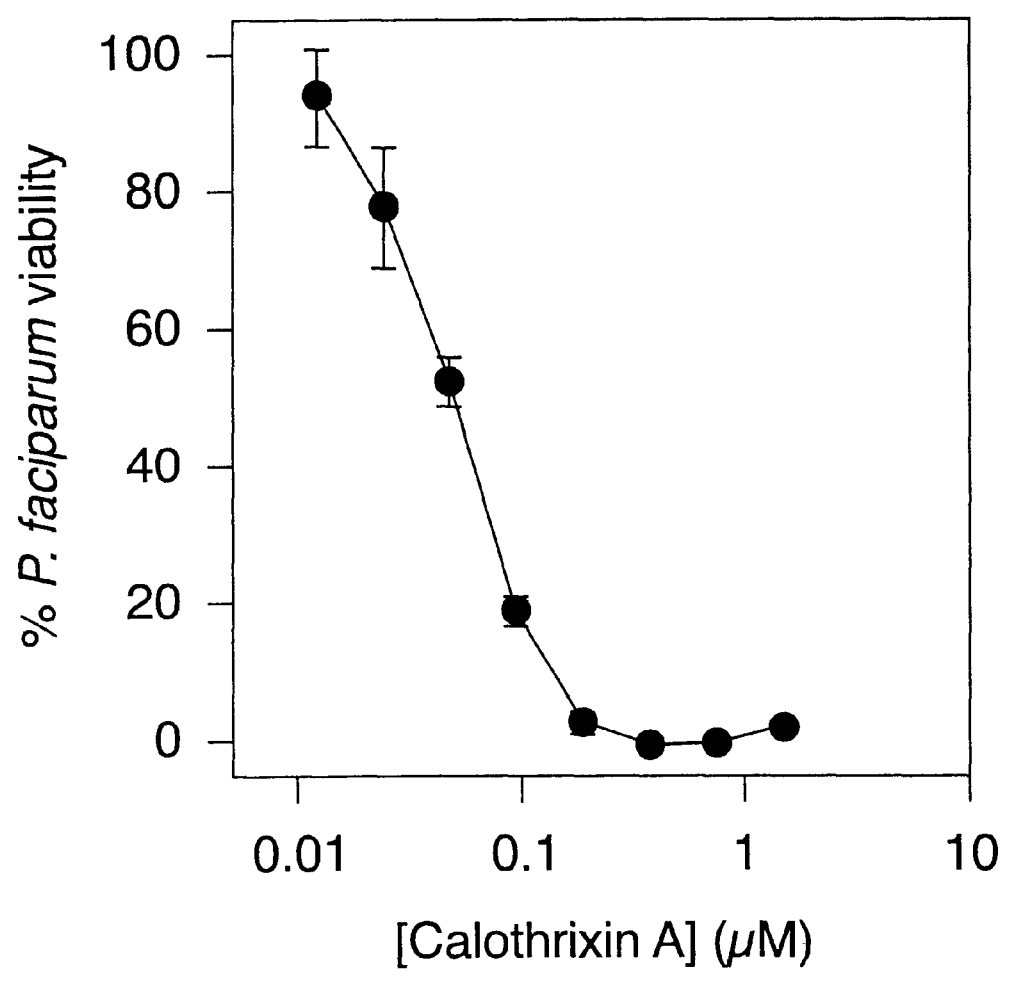

FIG. 1 graphically depicts the dose-related effect of Calothrixin A on the growth of the malaria parasite *Plasmodium falciparum*.

EXAMPLES

Example 1

Production and Isolation of the Calothrixins

Figure 2:
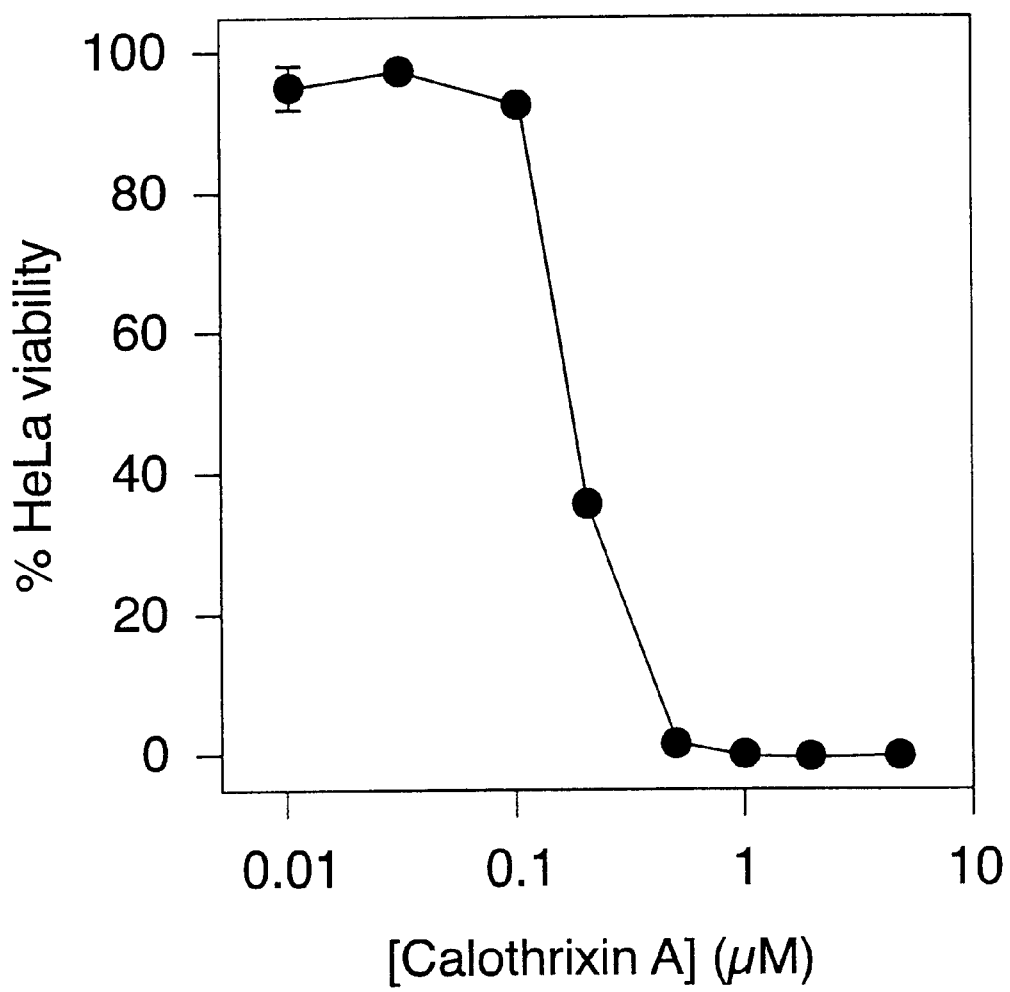
FIG. 2 graphically depicts the dose-related effect of Calothrixin A on the growth of HeLa cells.

The two bioactive Calothrix strains CAN 95/2 (Accession No NM99/03484) and CAN 95/3, (Schlegel, I., Doan, N. T., de Chazal, N. M. & Smith, G. D., *J. Appl. Phycol.* 10 471–479 (1998)) were collected in the Australian Capital Territory. They were grown photoautotrophically under nitrogen-fixing conditions.

In a particular example lyophilised cells (from CAN 95/2) (2.6 g) were extracted with ethyl acetate, using either large volumes of cold solvent or preferably Soxhlet conditions. Evaporation of the solvent afforded a wine-red residue, which was extracted with hexane to remove chlorophyll and lipids. Extraction of the residue with several small portions of acetone preferentially removed the more soluble calothrixin B (12 mg), leaving calothrixin A (47 mg) as an amorphous wine-red powder. Vacuum sublimation (180°/$10^{-2}$ mm Hg) of the acetone-extracted material afforded calothrixin B. Calothrixin A formed wine-red needles from DMSO, dec. 280° C. $\lambda_{max}$ (EtOH or EtOH+HCl) 292, 362 and 413 nm ($\epsilon$ 19000, 4260, 3100), $\lambda_{max}$ (EtOH+NaOH) 291, 310 (sh), 357 and 484 nm ($\epsilon$ 14900, 12100, 7820, 9680, 2050); HREIMS m/z 314.0695, 298.0747, 270.0790, 242.0841 and 214.0658 ($C_{19}H_{10}N_2O_3$, $C_{19}H_{10}N_2O_2$, $C_{18}H_{10}N_2O$, $C_{17}H_{10}N_2$ and $C_{16}H_8N$ require respectively m/z 314.0691, 298.0742, 270.0793, 242.0840, 214.0657). Calothrixin B showed $\lambda_{max}$ (EtOH or EtOH+HCl) 283, 352 and 405 nm ($\epsilon$ 15000, 2900, 1710), $\lambda_{max}$ (EtOH+NaOH) 290, 330, (sh) and 469 nm ($\epsilon$ 12500, 8080, 1520); EIMS m/z 298.0744 ($C_{19}H_{10}N_2O_2$ requires m/z 298.0742) 270, 242 and 214.

NMR data for Calothrixin A and B is presented below in Table 3.

TABLE 3

$^{13}$C and $^1$H NMR data from calothrixins A and B[a]

| Position | Calothrixin A | | Calothrixin B | |
|---|---|---|---|---|
| | $^{13}C^b$ | $^1H^d$ | $^{13}C^c$ | $^1H^d$ |
| CH-1 | 128.2 | 9.68 (bd) | 127.0 | 9.57 (d) |
| CH-2 | 132.0 | 7.98 (m) | 130.1 | 7.87 (t) |
| CH-3 | 132.1 | 7.96 (m) | 131.3 | 7.94 (t) |
| CH-4 | 119.2 | 8.60 (bd) | 129.7 | 8.16 (bd) |
| C-4a | 143.1 | | 151.2 | |
| CH-6 | 131.9 | 8.88 (s) | 147.6 | 9.61 (s) |
| C-6a | 130.0 | | 132.8 | |
| C-7 | 178.4 | | 180.5 | |
| C-7a | 115.2 | | 115.7 | |
| C-7b | 123.6 | | 123.6 | |
| CH-8 | 122.1 | 8.11 (bd) | 122.1 | 8.16 (bd) |
| CH-9 | 124.6 | 7.37 (bt) | 124.1 | 7.36 (t) |
| CH-10 | 127.1 | 7.44 (dt) | 126.8 | 7.44 (t) |
| CH-11 | 114.2 | 7.60 (bd) | 114.2 | 7.61 (d) |
| C-11a | 138.4[e] | | 139.0 | |
| C-12a | 139.0[e] | | N.c. | |
| C-13 | 177.9 | | N.c. | |
| C-13a | 122.1 | | 125.0 | |
| C-13b | 126.9 | | 122.7 | |
| NH | | 13.2 (b) | | |

[a]Spectra recorded for solutions in $D_6$-DMSO, referenced to solvent, at 500 or 600 MHz for $^1$H and 125.75 or 150.87 MHz for $^{13}$C.
[b]Derived from direct APT $^{13}$C observation data, and assigned from HMQC and HMBC.
[c]Derived and assigned from indirect $^1$H observation data (HMQC and HMBC).
[d]b broad, d doublet, m multiplet, s singlet, t triplet.
[e]Assignments may be interchanged.
N.c No correlation observed and hence not identified.

Example 2

Preparation of N-methyl Calothrixin A

Calothrixin A (0.3 mg) was stirred with anhydrous potassium carbonate (2.5 mg) and methyl iodide (0.2 ml) in a stoppered vial at room temperature for 2 days. Work-up in the usual way afforded N-methyl calothrixin A; HREIMS m/z 328.0847 and 312.0901 ($C_{20}H_{12}N_2O_3$ and $C_{20}H_{12}N_2O_2$ require respectively 328.0848 and 312.0898).

Example 3

Chloroquine-resistant Malaria Parasite

A chloroquine-resistant strain (FAF6, derived from ITG2 strain (Biggs, B. A., Gooze, L., Wycherley, K., Wollish, W., Southwell, B., Leech, J. H., and Brown, G. V (1991). *Proc. Natl. Acad. Sci.* USA 88, 9171–9174, 1991) of the malaria parasite. *Plasmodium falciparum* was used. Parasites were cultured in standard media (Trager, W. and Jensen, J. B. (1976). Science 193 673–675) with modifications (Cranmer, S. L., Magowan, C., Lian, J., Coppel, R. L., and Cooke, B. M. (1997). *Trans. Roy. Soc. Trop. Med. Hyg.* 91, 363–365). At the start of the assay the parasitaemia was 2% and haematocrit was 2%. Parasites were incubated in the presence of inhibitors in 96-well plates for 48 h.

Parasite-derived lactate dehydrogenase activity at the end of the 48 h period was used as a measure of parasite viability in vitro (Makler, M. T., Ries, J. M., Williams, J. A., Bancroft, J. E., Piper, R. C., Gibbins, B. L., and Hinrichs, D. J. (1993). *Am. J. Trop. Med. Hyg.* 48, 739–741).

The results are illustrated in FIG. 1.

Example 4

Assay Method for HeLa Cells

Exponentially growing HeLa cells were trysinized, centrifuged and resuspended in fresh medium. (RPMI 1640, 20% FCS, 2 mM glutamine). Cell suspension (100 $\mu$L) was aliquotted into 96 well microtitre plates at a seeding density previously demonstrated to allow exponential growth for 4 days. Calothrix cell extracts or the purified active compound were prepared in dimethyl sulphoxide, serially diluted in complete medium, then added (100 $\mu$L) in quadruplicate to cell suspensions. Cells were incubated continuously with extracts at 37° C. for 4 days. Cytotoxicity was determined using the MTT [3-(4,5dimethylthiazol-2-yl)-2,5-diphenyltetrazolium bromide] assay. MTT (50 $\mu$L, 2 mg ML$^{-1}$) was aliquotted into all wells of the microtitre plate and incubated at 37° C. for 4 h. Plates were inverted to discard medium and formazan crystals were solubilized in 100 $\mu$L DMSO with 25 $\mu$L glycine buffer (0.1 M glycine in 0.1 M NaCl, pH 10.5). Plates were agitated for 30 s and absorbances determined immediately at 540 nM using a Titertek Multiskan Plus MKII ELISA plate reader.

Figure 3:
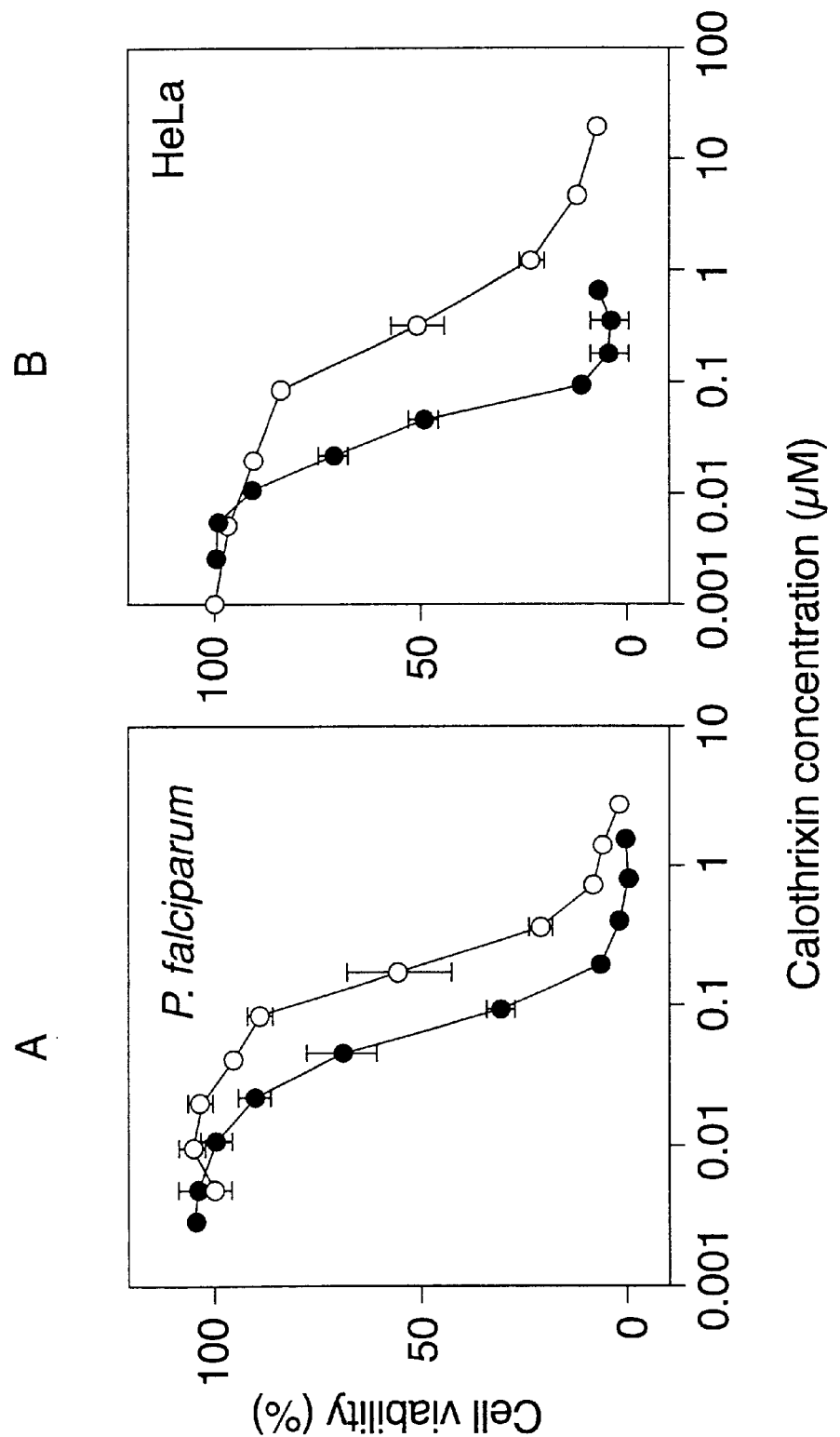
FIG. 3 graphically depicts dose response curves for Calothrixins A ( ) and B(o) against cultures of the malaria parasite *P. Falcipanum* and HeLa cells.

The results are illustrated in FIG. 2. Comparative results for Calothrixin A and B are shown in FIG. 3.

Example 5

Inhibition of DNA Replication by Calothrixin A
Cell Growth Inhibition Assays The inhibitory effects of the compounds were measured quantitatively by microtitre plate assays. For the non-photosynthetic bacteria and fungi, cell growth was measured with a plate reader as the culture turbidity at the wavelength 630 nm. For the photosynthetic organisms, a wavelength of 405 nm was used. For the mice myeloma cell culture, a colourimetric assay was used for the quantification of cell viability based on cleavage of the tetrazolium salt WST-1 (purchased from Boehringer Mannheim) by mitochondrial dehydrogenases in viable cells (Liu et al., 1995). The absence of an effect of calothixin on hepatocytes was judged by visual inspection for intactness of cells. For the observations of the bacteriocidal or bacteriostatic effects of the bioactive compounds, the turbidity and viable cell numbers of cultures of *Bacillus subtilis* (30 mL), grown in glucose minimal medium in Erlenmeyer flasks, were measured at different periods after the addition of the compounds.

In vivo Assays of DNA, RNA and Protein Synthesis

The biosyntheses of DNA, RNA and protein were estimated from the radioactivities incorporated into trichloroacetic acid (TCA)-insoluble fractions, using as substrates [$^3$H]thymidine (final concentration 0.4 $\mu$Ci mL$^{-1}$), [$^3$H] uracil (0.1 $\mu$Ci mL$^{-1}$) and [$^{14}$C]leucine (0.025 $\mu$Ci mL$^{-1}$), respectively. The leucine isotope was purchased from Amershan, while the thymidine and uracil isotopes were purchased from ICN.

For such assays the usual test organism is an *Escherichia coli* mutant that cannot synthesize its own thymine. Because of the inability of calothrixin A to kill G-bacteria, however, a thyA$^-$ of *Bacillus subtilis* was used (strain 168, trp C2 thyA thyB; kindly provided by Professor Gerry Wake). It was grown overnight in LB medium at 37° C. with aeration, diluted 1/5 with fresh Glucose Minimal Medium (GMM), supplemented with tryptophane (50 $\mu$g mL$^{-1}$) and thymine (20 $\mu$g mL$^{-1}$), and then incubated at 37° C. with aeration overnight. The overnight culture was diluted 1/19 with fresh GMM, incubated at 37° C. with aeration for 4 h, and then another volume of fresh GMM medium added and incubation continued at 37° C. with aeration for another 2 h (the culture being then at the mid-exponential phase of growth, with $A_{600}$ approximately 0.5). To the exponentially growing culture (4 mL), isotope solution (0.5 mL) calothrixin A solution (0.5 mL) were, added, and the mixture incubated at 37° C. with aeration. Samples (1 mL) were taken after 0, 10, 20, 30 min and added to 0.5 mL of 20% TCA solution in test tubes, then placed on ice for 30 min. The acid-insoluble contents were collected on Whatman GF/C glass fibre filters (pore size 1.2 $\mu$m) and washed with 5% TCA solution (40 mL) containing 1 mM each of thymidine, uracil, and leucine, followed by absolute ethanol (20 mL), and then dried. To the filters were added Packard, Starscint scintillation fluid (6 mL) and the radioactivity counted in a Beckman LS 6500 scintillation counter.

In vitro Transcription Assays

For transcription assays, the Riboprobe in vitro "Tranrcription Systems" (Promega) was used, with *E.coli* RNA polymerase purchased from Boehringer-Mannheim. [$^3$H] UTP (specific activity 45 Ci mmol$^{-1}$) was purchased from Amersham. The reaction mixture contained Transcription Optimized ×5 buffer (4 $\mu$l), DTT (10 mM), genomic DNA (as stated), RNase inhibitor (20 U), *E.coli* RNA polymerase (as stated), 0.66 mM each of rATP, rGTP and rCTP, 12 $\mu$M rUTP and 0.05 $\mu$Ci of [$^3$H]UTP. Genomic DNA was purified from *E.coli* strain DG17 (Sevastopoulos et al., *Proc Nat Acad Sci USA* 74; 3485–891977) by the Wizard Genomic DNA Purification Kit (Promega). The purity and concentration, of DNA templates was checked by agarose gel electrophoresis and the absorbance measured quantitatively using an Hitachi U-1100 spectrophotometer. For inhibition measurements, calothrixin A was incubated with the polymerase and DNA prior to addition of rNTP. The final reaction mixture (20 $\mu$L) was incubated at 37° C. for 20 min.

Incorporation of the radio-labelled rUTP, was determined after TCA precipitation. At the end of the incubations, samples (15 $\mu$L) of the reaction mixture were taken and the reactions stopped by adding 100 $\mu$L of carrier nucleic acid tRNA (1 $\mu$g L$^{-1}$, Sigma) and 0.5 mL of ice-cold TCA solution (5% w/v). The precipitates were collected on pre-wetted Whatman GF/C glass fibre filter disks. The filters were washed twice with 5% TCA (20 mL) to remove unincorporated rUTP isotope, followed by acetone (15 mL); and then air dried and placed in vials containing scintillation fluid (Starscint, Packard, 6 mL). The activity was measured using a Beckman LS 6500 scintillation counter. For estimation of total counts, a second aliquot (2 $\mu$L) of the reaction mixture was spotted on to a Whatman GF/A glass fibre filter disk, dried, and the radioactivity measured. The total counts and TCA precipitable counts were used to calculate the percentage incorporation of radio-labelled rUTP.

In vitro Transcription Assays

Figure 5:
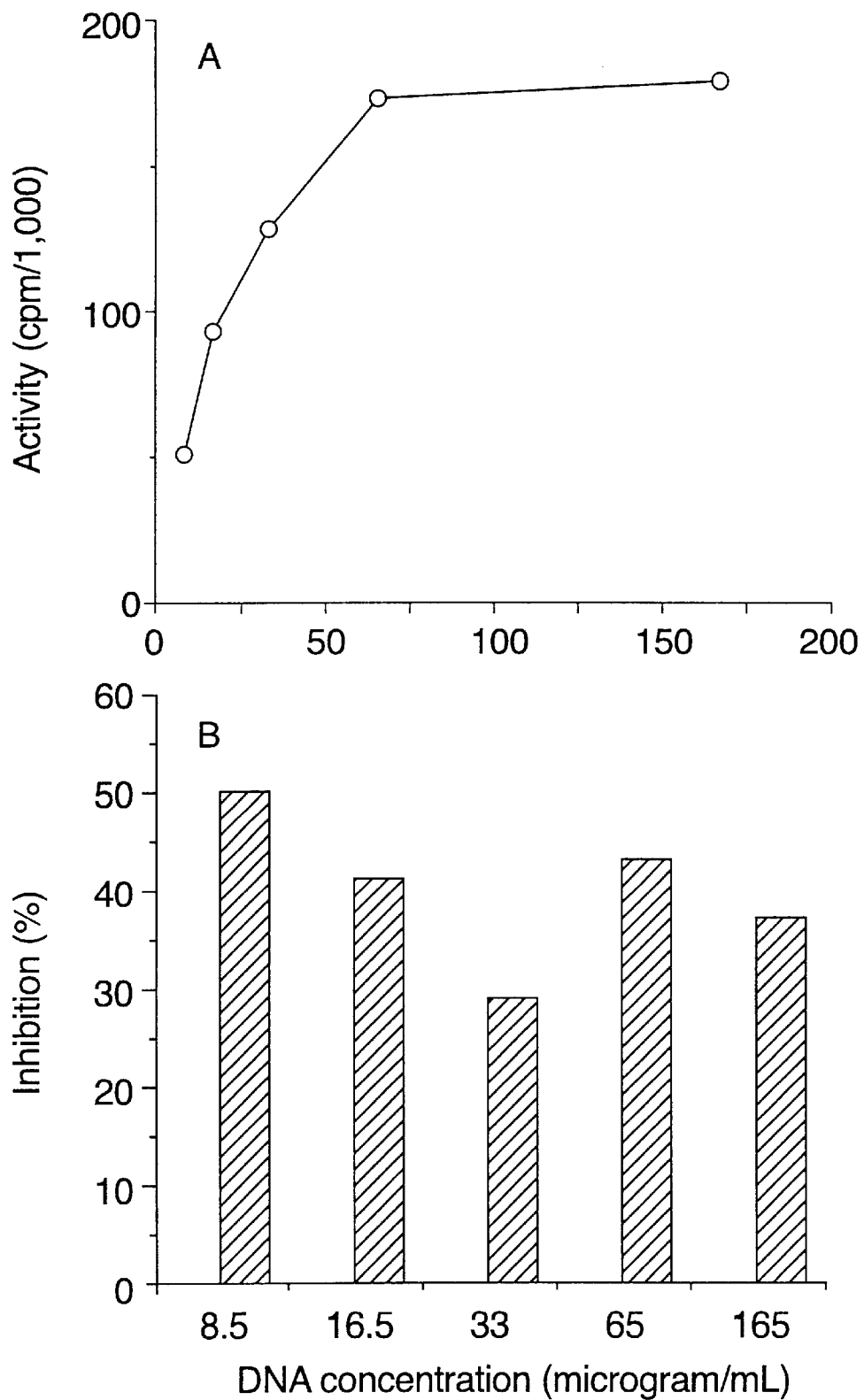

The percentage inhibition of RNA synthesis by fixed concentrations of calothrixin A (100 $\mu$M) remained relatively constant over a range of DNA concentrations (FIG. 5). The DNA concentrations were chosen to cover a range of reaction rates across the saturation curves measured in control assays (FIG. 5A). In these assays the amount of polymerase was kept constant (0.5 units per reaction). This result suggests that the compound does not act primarily on the DNA template, but on the enzyme.

The the mutant strain i B.subtilis 168 was chosen for studies of the compound at the whole cell level because, although the calothrixin A $IC_{50}$ was two orders of magnitude greater than that for plasmodium or HeLa cells, *B.subtilis* nevertheless was inhibited by the compound at conveniently low concentrations. Moreover, use of the mutant facilitated a study of the incorporation of external thymine/thymidine, which is, less readily taken up into DNA by wild type strains.

Figure 4:
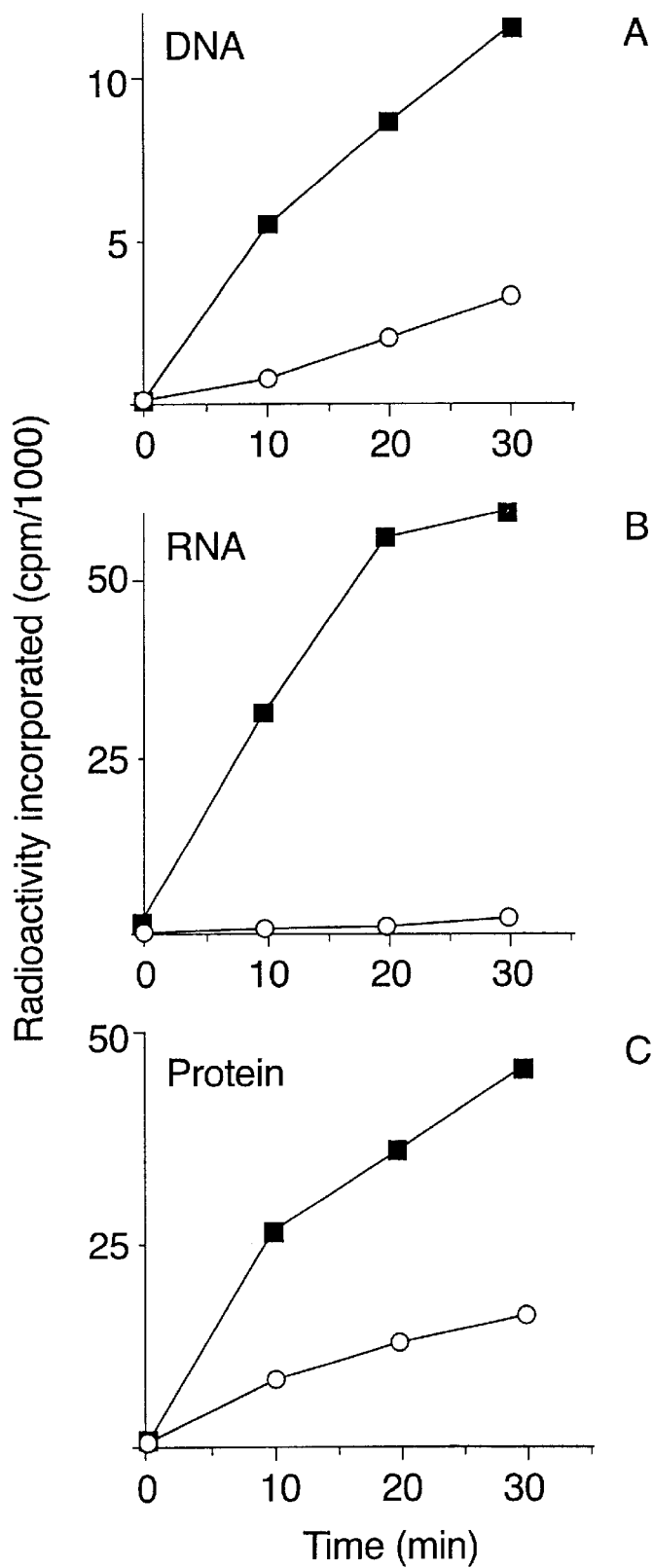
FIG. 4 depicts the effects of Calothrixin A (o) (16 micromolar) on the incorporation of radio-labelled [$^3$H]thymidine, [$^3$H]uracil and [$^{14}$C]leucine into the DNA, RNA and protein fractions of *Bacillus, subtilis* 168 compared with controls ( FIG. 5 depicts the relationship between the DNA template concentration and the rate of in vitro RNA synthesis in (A) control assays, with (o) DMSO added and (B) inhibition assays with 100 uM Calothrixin A. Each reaction contained 0.5 U of *E. Coli* RNA polymerase and the rates refer to incorporation of [$^3$H]UTP into RNA molecules. Calothrixin was dissolved in DMSO.
Figure 6:
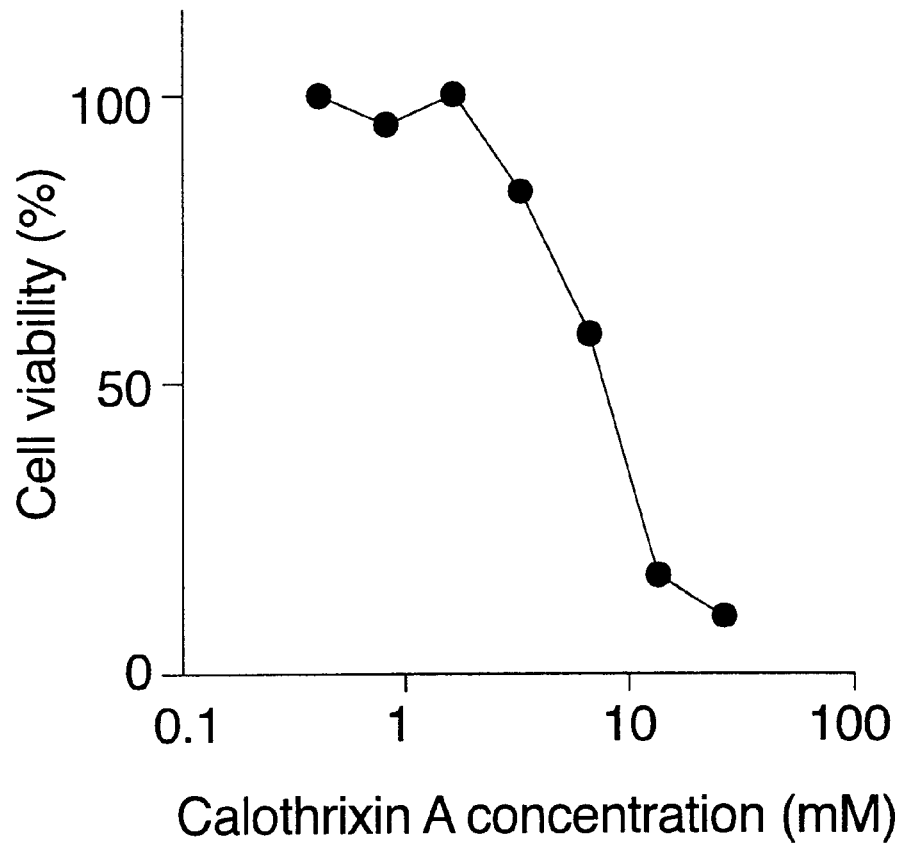
FIG. 6 depicts the dose response curve for Calothrixin A against a culture of *B subtilis* 168

Results are shown in FIGS. 4–6

Example 6

Further compounds of Formula (1) and (II) are depicted in Tables A and B

TABLE B

Formula II (N-oxide or free base)

| m | n | R | $R^4$ | $R^5$ | Y | Z |
|---|---|---|---|---|---|---|
| 0 | 0 | H | OH | OH | — | — |
| 0 | 0 | Me | OH | OH | — | — |
| 0 | 0 | Et | OH | OH | — | — |
| 0 | 0 | Ac | OH | OH | — | — |
| 1 | 0 | H | OH | OH | Br | — |
| 1 | 0 | H | OH | OH | Cl | — |
| 1 | 0 | H | OH | OH | I | — |
| 1 | 0 | H | OH | OH | Ac | — |
| 1 | 0 | H | OH | OH | $SO_3H$ | — |
| 1 | 0 | H | OH | OH | Me | — |
| 1 | 0 | H | OH | OH | Et | — |
| 1 | 0 | H | OH | OH | Pr | — |
| 1 | 0 | H | OH | OH | $NO_2$ | — |
| 1 | 0 | H | OH | OH | $CO_2H$ | — |
| 1 | 0 | H | OH | OH | $CO_2Me$ | — |
| 1 | 0 | H | OH | OH | $CO_2Et$ | — |
| 1 | 0 | H | OH | OH | $CO_2Pr$ | — |
| 1 | 0 | H | OH | OH | $CONH_2$ | — |
| 1 | 0 | H | OH | OH | CN | — |
| 1 | 0 | H | OH | OH | OH | — |
| 1 | 0 | H | OH | OH | $NH_2$ | — |
| 1 | 0 | H | OH | OH | NHMe | — |
| 1 | 0 | H | OH | OH | NHEt | — |
| 1 | 0 | H | OH | OH | NHPr | — |
| 1 | 0 | H | OH | OH | NHAc | — |
| 1 | 0 | H | OH | OH | CHO | — |
| 1 | 0 | Me | OH | OH | Br | — |
| 1 | 0 | Me | OH | OH | Cl | — |
| 1 | 0 | Me | OH | OH | I | — |
| 1 | 0 | Me | OH | OH | Ac | — |
| 1 | 0 | Me | OH | OH | $SO_3H$ | — |
| 1 | 0 | Me | OH | OH | Me | — |
| 1 | 0 | Me | OH | OH | Et | — |
| 1 | 0 | Me | OH | OH | Pr | — |
| 1 | 0 | Me | OH | OH | $NO_2$ | — |
| 1 | 0 | Me | OH | OH | $CO_2H$ | — |
| 1 | 0 | Me | OH | OH | $CO_2Me$ | — |
| i | 0 | Me | OH | OH | $CO_2Et$ | — |
| 1 | 0 | Me | OH | OH | $CO_2Pr$ | — |
| 1 | 0 | Me | OH | OH | $CONH_2$ | — |
| 1 | 0 | Me | OH | OH | CN | — |
| 1 | 0 | Me | OH | OH | OH | — |
| 1 | 0 | Me | OH | OH | $NH_2$ | — |
| 1 | 0 | Me | OH | OH | NHMe | — |
| 1 | 0 | Me | OH | OH | NHEt | — |
| 1 | 0 | Me | OH | OH | NHPr | — |
| 1 | 0 | Me | OH | OH | NHAc | — |
| 1 | 0 | Me | OH | OH | CHO | — |
| 1 | 0 | Et | OH | OH | Br | — |
| 1 | 0 | Et | OH | OH | Cl | — |
| 1 | 0 | Et | OH | OH | I | — |
| 1 | 0 | Et | OH | OH | Ac | — |
| 1 | 0 | Et | OH | OH | $SO_3H$ | — |
| 1 | 0 | Et | OH | OH | Me | — |
| 1 | 0 | Et | OH | OH | Et | — |
| 1 | 0 | Et | OH | OH | Pr | — |
| 1 | 0 | Et | OH | OH | $NO_2$ | — |
| 1 | 0 | Et | OH | OH | $CO_2H$ | — |
| 1 | 0 | Et | OH | OH | $CO_2Me$ | — |
| 1 | 0 | Et | OH | OH | $CO_2Et$ | — |
| 1 | 0 | Et | OH | OH | $CO_2Pr$ | — |
| 1 | 0 | Et | OH | OH | $CONH_2$ | — |
| 1 | 0 | Et | OH | OH | CN | — |
| 1 | 0 | Et | OH | OH | OH | — |
| 1 | 0 | Et | OH | OH | $NH_2$ | — |
| 1 | 0 | Et | OH | OH | NHMe | — |
| 1 | 0 | Et | OH | OH | NHEt | — |
| 1 | 0 | Et | OH | OH | NHPr | — |
| 1 | 0 | Et | OH | OH | NHAc | — |
| 1 | 0 | Et | OH | OH | CHO | — |
| 1 | 0 | Ac | OH | OH | Br | — |
| 1 | 0 | Ac | OH | OH | Cl | — |
| 1 | 0 | Ac | OH | OH | I | — |
| 1 | 0 | Ac | OH | OH | Ac | — |
| 1 | 0 | Ac | OH | OH | $SO_3H$ | — |
| 1 | 0 | Ac | OH | OH | Me | — |
| 1 | 0 | Ac | OH | OH | Et | — |
| 1 | 0 | Ac | OH | OH | Pr | — |
| 1 | 0 | Ac | OH | OH | $NO_2$ | — |
| 1 | 0 | Ac | OH | OH | $CO_2H$ | — |
| 1 | 0 | Ac | OH | OH | $CO_2Me$ | — |
| 1 | 0 | Ac | OH | OH | $CO_2Et$ | — |
| 1 | 0 | Ac | OH | OH | $CO_2Pr$ | — |
| 1 | 0 | Ac | OH | OH | $CONH_2$ | — |
| 1 | 0 | Ac | OH | OH | CN | — |
| 1 | 0 | Ac | OH | OH | OH | — |
| 1 | 0 | Ac | OH | OH | $NH_2$ | — |
| 1 | 0 | Ac | OH | OH | NHMe | — |
| 1 | 0 | Ac | OH | OH | NHEt | — |
| 1 | 0 | Ac | OH | OH | NHPr | — |
| 1 | 0 | Ac | OH | OH | NHAc | — |
| 1 | 0 | Ac | OH | OH | CHO | — |
| 0 | 1 | H | OH | OH | — | Br |
| 0 | 1 | H | OH | OH | — | Cl |
| 0 | 1 | H | OH | OH | — | I |
| 0 | 1 | H | OH | OH | — | Ac |
| 0 | 1 | H | OH | OH | — | $SO_3H$ |
| 0 | 1 | H | OH | OH | — | Me |
| 0 | 1 | H | OH | OH | — | Et |
| 0 | 1 | H | OH | OH | — | Pr |
| 0 | 1 | H | OH | OH | — | $NO_2$ |
| 0 | 1 | H | OH | OH | — | $CO_2H$ |
| 0 | 1 | H | OH | OH | — | $CO_2Me$ |
| 0 | 1 | H | OH | OH | — | $CO_2Et$ |
| 0 | 1 | H | OH | OH | — | $CO_2Pr$ |
| 0 | 1 | H | OH | OH | — | $CONH_2$ |
| 0 | 1 | H | OH | OH | — | CN |
| 0 | 1 | H | OH | OH | — | OH |
| 0 | 1 | H | OH | OH | — | $NH_2$ |
| 0 | 1 | H | OH | OH | — | NHMe |
| 0 | 1 | H | OH | OH | — | NHEt |
| 0 | 1 | H | OH | OH | — | NHPr |
| 0 | 1 | H | OH | OH | — | NHAc |
| 0 | 1 | H | OH | OH | — | CHO |
| 0 | 1 | Me | OH | OH | — | Br |
| 0 | 1 | Me | OH | OH | — | Cl |
| 0 | 1 | Me | OH | OH | — | I |
| 0 | 1 | Me | OH | OH | — | Ac |
| 0 | 1 | Me | OH | OH | — | $SO_3H$ |
| 0 | 1 | Me | OH | OH | — | Me |
| 0 | 1 | Me | OH | OH | — | Et |
| 0 | 1 | Me | OH | OH | — | Pr |
| 0 | 1 | Me | OH | OH | — | $NO_2$ |
| 0 | 1 | Me | OH | OH | — | $CO_2H$ |
| 0 | 1 | Me | OH | OH | — | $CO_2Me$ |
| 0 | 1 | Me | OH | OH | — | $CO_2Et$ |
| 0 | 1 | Me | OH | OH | — | $CO_2Pr$ |
| 0 | 1 | Me | OH | OH | — | $CONH_2$ |
| 0 | 1 | Me | OH | OH | — | CN |
| 0 | 1 | Me | OH | OH | — | OH |
| 0 | 1 | Me | OH | OH | — | $NH_2$ |

TABLE B-continued

Formula II (N-oxide or free base)

| m | n | R | R⁴ | R⁵ | Y | Z |
|---|---|---|----|----|---|---|
| 0 | 1 | Me | OH | OH | — | NHMe |
| 0 | 1 | Me | OH | OH | — | NHEt |
| 0 | 1 | Me | OH | OH | — | NHPr |
| 0 | 1 | Me | OH | OH | — | NHAc |
| 0 | 1 | Me | OH | OH | — | CHO |
| 0 | 1 | Et | OH | OH | — | Br |
| 0 | 1 | Et | OH | OH | — | Cl |
| 0 | 1 | Et | OH | OH | — | I |
| 0 | 1 | Et | OH | OH | — | Ac |
| 0 | 1 | Et | OH | OH | — | SO₃H |
| 0 | 1 | Et | OH | OH | — | Me |
| 0 | 1 | Et | OH | OH | — | Et |
| 0 | 1 | Et | OH | OH | — | Pr |
| 0 | 1 | Et | OH | OH | — | NO₂ |
| 0 | 1 | Et | OH | OH | — | CO₂H |
| 0 | 1 | Et | OH | OH | — | CO₂Me |
| 0 | 1 | Et | OH | OH | — | CO₂Et |
| 0 | 1 | Et | OH | OH | — | CO₂Pr |
| 0 | 1 | Et | OH | OH | — | CONH₂ |
| 0 | 1 | Et | OH | OH | — | CN |
| 0 | 1 | Et | OH | OH | — | OH |
| 0 | 1 | Et | OH | OH | — | NH₂ |
| 0 | 1 | Et | OH | OH | — | NHMe |
| 0 | 1 | Et | OH | OH | — | NHEt |
| 0 | 1 | Et | OH | OH | — | NHPr |
| 0 | 1 | Et | OH | OH | — | NHAc |
| 0 | 1 | Et | OH | OH | — | CHO |
| 0 | 1 | Ac | OH | OH | — | Br |
| 0 | 1 | Ac | OH | OH | — | Cl |
| 0 | 1 | Ac | OH | OH | — | I |
| 0 | 1 | Ac | OH | OH | — | Ac |
| 0 | 1 | Ac | OH | OH | — | SO₃H |
| 0 | 1 | Ac | OH | OH | — | Me |
| 0 | 1 | Ac | OH | OH | — | Et |
| 0 | 1 | Ac | OH | OH | — | Pr |
| 0 | 1 | Ac | OH | OH | — | NO₂ |
| 0 | 1 | Ac | OH | OH | — | CO₂H |
| 0 | 1 | Ac | OH | OH | — | CO₂Me |
| 0 | 1 | Ac | OH | OH | — | CO₂Et |
| 0 | 1 | Ac | OH | OH | — | CO₂Pr |
| 0 | 1 | Ac | OH | OH | — | CONH₂ |
| 0 | 1 | Ac | OH | OH | — | CN |
| 0 | 1 | Ac | OH | OH | — | OH |
| 0 | 1 | Ac | OH | OH | — | NH₂ |
| 0 | 1 | Ac | OH | OH | — | NHMe |
| 0 | 1 | Ac | OH | OH | — | NHEt |
| 0 | 1 | Ac | OH | OH | — | NHPr |
| 0 | 1 | Ac | OH | OH | — | NHAc |
| 0 | 1 | Ac | OH | OH | — | CHO |
| 1 | 1 | H | OH | OH | Br | Br |
| 1 | 1 | H | OH | OH | Cl | Cl |
| 1 | 1 | H | OH | OH | I | I |
| 1 | 1 | H | OH | OH | Ac | Ac |
| 1 | 1 | H | OH | OH | SO₃H | SO₃H |
| 1 | 1 | H | OH | OH | Me | Me |
| 1 | 1 | H | OH | OH | Et | Et |
| 1 | 1 | H | OH | OH | Pr | Pr |
| 1 | 1 | H | OH | OH | NO₂ | NO₂ |
| 1 | 1 | H | OH | OH | CO₂H | CO₂H |
| 1 | 1 | H | OH | OH | CO₂Me | CO₂Me |
| 1 | 1 | H | OH | OH | CO₂Et | CO₂Et |
| 1 | 1 | H | OH | OH | CO₂Pr | CO₂Pr |
| 1 | 1 | H | OH | OH | CONH₂ | CONH₂ |
| 1 | 1 | H | OH | OH | CN | CN |
| 1 | 1 | H | OH | OH | OH | OH |
| 1 | 1 | H | OH | OH | NH₂ | NH₂ |
| 1 | 1 | H | OH | OH | NHMe | NHMe |
| 1 | 1 | H | OH | OH | NHEt | NHEt |
| 1 | 1 | H | OH | OH | NHPr | NHPr |
| 1 | 1 | H | OH | OH | NHAc | NHAc |
| 1 | 1 | H | OH | OH | CHO | CHO |
| 1 | 1 | Me | OH | OH | Br | Br |
| 1 | 1 | Me | OH | OH | Cl | Cl |
| 1 | 1 | Me | OH | OH | I | I |
| 1 | 1 | Me | OH | OH | Ac | Ac |
| 1 | 1 | Me | OH | OH | SO₃H | SO₃H |
| 1 | 1 | Me | OH | OH | Me | Me |
| 1 | 1 | Me | OH | OH | Et | Et |
| 1 | 1 | Me | OH | OH | Pr | Pr |
| 1 | 1 | Me | OH | OH | NO₂ | NO₂ |
| 1 | 1 | Me | OH | OH | CO₂H | CO₂H |
| 1 | 1 | Me | OH | OH | CO₂Me | CO₂Me |
| 1 | 1 | Me | OH | OH | CO₂Et | CO₂Et |
| 1 | 1 | Me | OH | OH | CO₂Pr | CO₂Pr |
| 1 | 1 | Me | OH | OH | CONH₂ | CONH₂ |
| 1 | 1 | Me | OH | OH | CN | CN |
| 1 | 1 | Me | OH | OH | OH | OH |
| 1 | 1 | Me | OH | OH | NH₂ | NH₂ |
| 1 | 1 | Me | OH | OH | NHMe | NHMe |
| 1 | 1 | Me | OH | OH | NHEt | NHEt |
| 1 | 1 | Me | OH | OH | NHPr | NHPr |
| 1 | 1 | Me | OH | OH | NHAc | NHAc |
| 1 | 1 | Me | OH | OH | CHO | CHO |
| 1 | 1 | Et | OH | OH | Br | Br |
| 1 | 1 | Et | OH | OH | Cl | Cl |
| 1 | 1 | Et | OH | OH | I | I |
| 1 | 1 | Et | OH | OH | Ac | Ac |
| 1 | 1 | Et | OH | OH | SO₃H | SO₃H |
| 1 | 1 | Et | OH | OH | Me | Me |
| 1 | 1 | Et | OH | OH | Et | Et |
| 1 | 1 | Et | OH | OH | Pr | Pr |
| 1 | 1 | Et | OH | OH | NO₂ | NO₂ |
| 1 | 1 | Et | OH | OH | CO₂H | CO₂H |
| 1 | 1 | Et | OH | OH | CO₂Me | CO₂Me |
| 1 | 1 | Et | OH | OH | CO₂Et | CO₂Et |
| 1 | 1 | Et | OH | OH | CO₂Pr | CO₂Pr |
| 1 | 1 | Et | OH | OH | CONH₂ | CONH₂ |
| 1 | 1 | Et | OH | OH | CN | CN |
| 1 | 1 | Et | OH | OH | OH | OH |
| 1 | 1 | Et | OH | OH | NH₂ | NH₂ |
| 1 | 1 | Et | OH | OH | NHMe | NHMe |
| 1 | 1 | Et | OH | OH | NHEt | NHEt |
| 1 | 1 | Et | OH | OH | NHPr | NHPr |
| 1 | 1 | Et | OH | OH | NHAc | NHAc |
| 1 | 1 | Et | OH | OH | CHO | CHO |
| 1 | 1 | Ac | OH | OH | Br | Br |
| 1 | 1 | Ac | OH | OH | Cl | Cl |
| 1 | 1 | Ac | OH | OH | I | I |
| 1 | 1 | Ac | OH | OH | Ac | Ac |
| 1 | 1 | Ac | OH | OH | SO₃H | SO₃H |
| 1 | 1 | Ac | OH | OH | Me | Me |
| 1 | 1 | Ac | OH | OH | Et | Et |
| 1 | 1 | Ac | OH | OH | Pr | Pr |
| 1 | 1 | Ac | OH | OH | NO₂ | NO₂ |
| 1 | 1 | Ac | OH | OH | CO₂H | CO₂H |
| 1 | 1 | Ac | OH | OH | CO₂Me | CO₂Me |
| 1 | 1 | Ac | OH | OH | CO₂Et | CO₂Et |
| 1 | 1 | Ac | OH | OH | CO₂Pr | CO₂Pr |
| 1 | 1 | Ac | OH | OH | CONH₂ | CONH₂ |
| 1 | 1 | Ac | OH | OH | CN | CN |
| 1 | 1 | Ac | OH | OH | OH | OH |
| 1 | 1 | Ac | OH | OH | NH₂ | NH₂ |
| 1 | 1 | Ac | OH | OH | NHMe | NHMe |
| 1 | 1 | Ac | OH | OH | NHEt | NHEt |
| 1 | 1 | Ac | OH | OH | NHPr | NHPr |
| 1 | 1 | Ac | OH | OH | NHAc | NHAc |
| 1 | 1 | Ac | OH | OH | CHO | CHO |
| 2 | 1 | H | OH | OH | Br | Br |
| 2 | 1 | H | OH | OH | Cl | Cl |
| 2 | 1 | H | OH | OH | I | I |
| 2 | 1 | H | OH | OH | Ac | Ac |
| 2 | 1 | H | OH | OH | SO₃H | SO₃H |
| 2 | 1 | H | OH | OH | Me | Me |
| 2 | 1 | H | OH | OH | Et | Et |
| 2 | 1 | H | OH | OH | Pr | Pr |
| 2 | 1 | H | OH | OH | NO₂ | NO₂ |
| 2 | 1 | H | OH | OH | CO₂H | CO₂H |
| 2 | 1 | H | OH | OH | CO₂Me | CO₂Me |
| 2 | 1 | H | OH | OH | CO₂Et | CO₂Et |
| 2 | 1 | H | OH | OH | CO₂Pr | CO₂Pr |

TABLE B-continued

Formula II (N-oxide or free base)

| m | n | R | R⁴ | R⁵ | Y | Z |
|---|---|---|---|---|---|---|
| 2 | 1 | H | OH | OH | CONH₂ | CONH₂ |
| 2 | 1 | H | OH | OH | CN | CN |
| 2 | 1 | H | OH | OH | OH | OH |
| 2 | 1 | H | OH | OH | NH₂ | NH₂ |
| 2 | 1 | H | OH | OH | NHMe | NHMe |
| 2 | 1 | H | OH | OH | NHEt | NHEt |
| 2 | 1 | H | OH | OH | NHPr | NHPr |
| 2 | 1 | H | OH | OH | NHAc | NHAc |
| 2 | 1 | H | OH | OH | CHO | CHO |
| 2 | 1 | Me | OH | OH | Br | Br |
| 2 | 1 | Me | OH | OH | Cl | Cl |
| 2 | 1 | Me | OH | OH | I | I |
| 2 | 1 | Me | OH | OH | Ac | Ac |
| 2 | 1 | Me | OH | OH | SO₃H | SO₃H |
| 2 | 1 | Me | OH | OH | Me | Me |
| 2 | 1 | Me | OH | OH | Et | Et |
| 2 | 1 | Me | OH | OH | Pr | Pr |
| 2 | 1 | Me | OH | OH | NO₂ | NO₂ |
| 2 | 1 | Me | OH | OH | CO₂H | CO₂H |
| 2 | 1 | Me | OH | OH | CO₂Me | CO₂Me |
| 2 | 1 | Me | OH | OH | CO₂Et | CO₂Et |
| 2 | 1 | Me | OH | OH | CO₂Pr | CO₂Pr |
| 2 | 1 | Me | OH | OH | CONH₂ | CONH₂ |
| 2 | 1 | Me | OH | OH | CN | CN |
| 2 | 1 | Me | OH | OH | OH | OH |
| 2 | 1 | Me | OH | OH | NH₂ | NH₂ |
| 2 | 1 | Me | OH | OH | NHMe | NHMe |
| 2 | 1 | Me | OH | OH | NHEt | NHEt |
| 2 | 1 | Me | OH | OH | NHPr | NHPr |
| 2 | 1 | Me | OH | OH | NHAc | NHAc |
| 2 | 1 | Me | OH | OH | CHO | CHO |
| 2 | 1 | Et | OH | OH | Br | Br |
| 2 | 1 | Et | OH | OH | Cl | Cl |
| 2 | 1 | Et | OH | OH | I | I |
| 2 | 1 | Et | OH | OH | Ac | Ac |
| 2 | 1 | Et | OH | OH | SO₃H | SO₃H |
| 2 | 1 | Et | OH | OH | Me | Me |
| 2 | 1 | Et | OH | OH | Et | Et |
| 2 | 1 | Et | OH | OH | Pr | Pr |
| 2 | 1 | Et | OH | OH | NO₂ | NO₂ |
| 2 | 1 | Et | OH | OH | CO₂H | CO₂H |
| 2 | 1 | Et | OH | OH | CO₂Me | CO₂Me |
| 2 | 1 | Et | OH | OH | CO₂Et | CO₂Et |
| 2 | 1 | Et | OH | OH | CO₂Pr | CO₂Pr |
| 2 | 1 | Et | OH | OH | CONH₂ | CONH₂ |
| 2 | 1 | Et | OH | OH | CN | CN |
| 2 | 1 | Et | OH | OH | OH | OH |
| 2 | 1 | Et | OH | OH | NH₂ | NH₂ |
| 2 | 1 | Et | OH | OH | NHMe | NHMe |
| 2 | 1 | Et | OH | OH | NHEt | NHEt |
| 2 | 1 | Et | OH | OH | NHPr | NHPr |
| 2 | 1 | Et | OH | OH | NHAc | NHAc |
| 2 | 1 | Et | OH | OH | CHO | CHO |
| 2 | 1 | Ac | OH | OH | Br | Br |
| 2 | 1 | Ac | OH | OH | Cl | Cl |
| 2 | 1 | Ac | OH | OH | I | I |
| 2 | 1 | Ac | OH | OH | Ac | Ac |
| 2 | 1 | Ac | OH | OH | SO₃H | SO₃H |
| 2 | 1 | Ac | OH | OH | Me | Me |
| 2 | 1 | Ac | OH | OH | Et | Et |
| 2 | 1 | Ac | OH | OH | Pr | Pr |
| 2 | 1 | Ac | OH | OH | NO₂ | NO₂ |
| 2 | 1 | Ac | OH | OH | CO₂H | CO₂H |
| 2 | 1 | Ac | OH | OH | CO₂Me | CO₂Me |
| 2 | 1 | Ac | OH | OH | CO₂Et | CO₂Et |
| 2 | 1 | Ac | OH | OH | CO₂Pr | CO₂Pr |
| 2 | 1 | Ac | OH | OH | CONH₂ | CONH₂ |
| 2 | 1 | Ac | OH | OH | CN | CN |
| 2 | 1 | Ac | OH | OH | OH | OH |
| 2 | 1 | Ac | OH | OH | NH₂ | NH₂ |
| 2 | 1 | Ac | OH | OH | NHMe | NHMe |
| 2 | 1 | Ac | OH | OH | NHEt | NHEt |
| 2 | 1 | Ac | OH | OH | NHPr | NHPr |
| 2 | 1 | Ac | OH | OH | NHAc | NHAc |
| 2 | 1 | Ac | OH | OH | CHO | CHO |
| 1 | 2 | H | OH | OH | Br | Br |
| 1 | 2 | H | OH | OH | Cl | Cl |
| 1 | 2 | H | OH | OH | I | I |
| 1 | 2 | H | OH | OH | Ac | Ac |
| 1 | 2 | H | OH | OH | SO₃H | SO₃H |
| 1 | 2 | H | OH | OH | Me | Me |
| 1 | 2 | H | OH | OH | Et | Et |
| 1 | 2 | H | OH | OH | Pr | Pr |
| 1 | 2 | H | OH | OH | NO₂ | NO₂ |
| 1 | 2 | H | OH | OH | CO₂H | CO₂H |
| 1 | 2 | H | OH | OH | CO₂Me | CO₂Me |
| 1 | 2 | H | OH | OH | CO₂Et | CO₂Et |
| 1 | 2 | H | OH | OH | CO₂Pr | CO₂Pr |
| 1 | 2 | H | OH | OH | CONH₂ | CONH₂ |
| 1 | 2 | H | OH | OH | CN | CN |
| 1 | 2 | H | OH | OH | OH | OH |
| 1 | 2 | H | OH | OH | NH₂ | NH₂ |
| 1 | 2 | H | OH | OH | NHMe | NHMe |
| 1 | 2 | H | OH | OH | NHEt | NHEt |
| 1 | 2 | H | OH | OH | NHPr | NHPr |
| 1 | 2 | H | OH | OH | NHAc | NHAc |
| 1 | 2 | H | OH | OH | CHO | CHO |
| 1 | 2 | Me | OH | OH | Br | Br |
| 1 | 2 | Me | OH | OH | Cl | Cl |
| 1 | 2 | Me | OH | OH | I | I |
| 1 | 2 | Me | OH | OH | Ac | Ac |
| 1 | 2 | Me | OH | OH | SO₃H | SO₃H |
| 1 | 2 | Me | OH | OH | Me | Me |
| 1 | 2 | Me | OH | OH | Et | Et |
| 1 | 2 | Me | OH | OH | Pr | Pr |
| 1 | 2 | Me | OH | OH | NO₂ | NO₂ |
| 1 | 2 | Me | OH | OH | CO₂H | CO₂H |
| 1 | 2 | Me | OH | OH | CO₂Me | CO₂Me |
| 1 | 2 | Me | OH | OH | CO₂Et | CO₂Et |
| 1 | 2 | Me | OH | OH | CO₂Pr | CO₂Pr |
| 1 | 2 | Me | OH | OH | CONH₂ | CONH₂ |
| 1 | 2 | Me | OH | OH | CN | CN |
| 1 | 2 | Me | OH | OH | OH | OH |
| 1 | 2 | Me | OH | OH | NH₂ | NH₂ |
| 1 | 2 | Me | OH | OH | NHMe | NHMe |
| 1 | 2 | Me | OH | OH | NHEt | NHEt |
| 1 | 2 | Me | OH | OH | NHPr | NHPr |
| 1 | 2 | Me | OH | OH | NHAc | NHAc |
| 1 | 2 | Me | OH | OH | CHO | CHO |
| 1 | 2 | Et | OH | OH | Br | Br |
| 1 | 2 | Et | OH | OH | Cl | Cl |
| 1 | 2 | Et | OH | OH | I | I |
| 1 | 2 | Et | OH | OH | Ac | Ac |
| 1 | 2 | Et | OH | OH | SO₃H | SO₃H |
| 1 | 2 | Et | OH | OH | Me | Me |
| 1 | 2 | Et | OH | OH | Et | Et |
| 1 | 2 | Et | OH | OH | Pr | Pr |
| 1 | 2 | Et | OH | OH | NO₂ | NO₂ |
| 1 | 2 | Et | OH | OH | CO₂H | CO₂H |
| 1 | 2 | Et | OH | OH | CO₂Me | CO₂Me |
| 1 | 2 | Et | OH | OH | CO₂Et | CO₂Et |
| 1 | 2 | Et | OH | OH | CO₂Pr | CO₂Pr |
| 1 | 2 | Et | OH | OH | CONH₂ | CONH₂ |
| 1 | 2 | Et | OH | OH | CN | CN |
| 1 | 2 | Et | OH | OH | OH | OH |
| 1 | 2 | Et | OH | OH | NH₂ | NH₂ |
| 1 | 2 | Et | OH | OH | NHMe | NHMe |
| 1 | 2 | Et | OH | OH | NHEt | NHEt |
| 1 | 2 | Et | OH | OH | NHPr | NHPr |
| 1 | 2 | Et | OH | OH | NHAc | NHAc |
| 1 | 2 | Et | OH | OH | CHO | CHO |
| 1 | 2 | Ac | OH | OH | Br | Br |
| 1 | 2 | Ac | OH | OH | Cl | Cl |
| 1 | 2 | Ac | OH | OH | I | I |
| 1 | 2 | Ac | OH | OH | Ac | Ac |
| 1 | 2 | Ac | OH | OH | SO₃H | SO₃H |
| 1 | 2 | Ac | OH | OH | Me | Me |
| 1 | 2 | Ac | OH | OH | Et | Et |
| 1 | 2 | Ac | OH | OH | Pr | Pr |
| 1 | 2 | Ac | OH | OH | NO₂ | NO₂ |

TABLE B-continued

Formula II (N-oxide or free base)

| m | n | R | R⁴ | R⁵ | Y | Z |
|---|---|---|----|----|---|---|
| 1 | 2 | Ac | OH | OH | CO₂H | CO₂H |
| 1 | 2 | Ac | OH | OH | CO₂Me | CO₂Me |
| 1 | 2 | Ac | OH | OH | CO₂Et | CO₂Et |
| 1 | 2 | Ac | OH | OH | CO₂Pr | CO₂Pr |
| 1 | 2 | Ac | OH | OH | CONH₂ | CONH₂ |
| 1 | 2 | Ac | OH | OH | CN | CN |
| 1 | 2 | Ac | OH | OH | OH | OH |
| 1 | 2 | Ac | OH | OH | NH₂ | NH₂ |
| 1 | 2 | Ac | OH | OH | NHMe | NHMe |
| 1 | 2 | Ac | OH | OH | NHEt | NHEt |
| 1 | 2 | Ac | OH | OH | NHPr | NHPr |
| 1 | 2 | Ac | OH | OH | NHAc | NHAc |
| 1 | 2 | Ac | OH | OH | CHO | CHO |
| 2 | 2 | H | OH | OH | Br | Br |
| 2 | 2 | H | OH | OH | Cl | Cl |
| 2 | 2 | H | OH | OH | I | I |
| 2 | 2 | H | OH | OH | Ac | Ac |
| 2 | 2 | H | OH | OH | SO₃H | SO₃H |
| 2 | 2 | H | OH | OH | Me | Me |
| 2 | 2 | H | OH | OH | Et | Et |
| 2 | 2 | H | OH | OH | Pr | Pr |
| 2 | 2 | H | OH | OH | NO₂ | NO₂ |
| 2 | 2 | H | OH | OH | CO₂H | CO₂H |
| 2 | 2 | H | OH | OH | CO₂Me | CO₂Me |
| 2 | 2 | H | OH | OH | CO₂Et | CO₂Et |
| 2 | 2 | H | OH | OH | CO₂Pr | CO₂Pr |
| 2 | 2 | H | OH | OH | CONH₂ | CONH₂ |
| 2 | 2 | H | OH | OH | CN | CN |
| 2 | 2 | H | OH | OH | OH | OH |
| 2 | 2 | H | OH | OH | NH₂ | NH₂ |
| 2 | 2 | H | OH | OH | NHMe | NHMe |
| 2 | 2 | H | OH | OH | NHEt | NHEt |
| 2 | 2 | H | OH | OH | NHPr | NHPr |
| 2 | 2 | H | OH | OH | NHAc | NHAc |
| 2 | 2 | H | OH | OH | CHO | CHO |
| 2 | 2 | Me | OH | OH | Br | Br |
| 2 | 2 | Me | OH | OH | Cl | Cl |
| 2 | 2 | Me | OH | OH | I | I |
| 2 | 2 | Me | OH | OH | Ac | Ac |
| 2 | 2 | Me | OH | OH | SO₃H | SO₃H |
| 2 | 2 | Me | OH | OH | Me | Me |
| 2 | 2 | Me | OH | OH | Et | Et |
| 2 | 2 | Me | OH | OH | Pr | Pr |
| 2 | 2 | Me | OH | OH | NO₂ | NO₂ |
| 2 | 2 | Me | OH | OH | CO₂H | CO₂H |
| 2 | 2 | Me | OH | OH | CO₂Me | CO₂Me |
| 2 | 2 | Me | OH | OH | CO₂Et | CO₂Et |
| 2 | 2 | Me | OH | OH | CO₂Pr | CO₂Pr |
| 2 | 2 | Me | OH | OH | CONH₂ | CONH₂ |
| 2 | 2 | Me | OH | OH | CN | CN |
| 2 | 2 | Me | OH | OH | OH | OH |
| 2 | 2 | Me | OH | OH | NH₂ | NH₂ |
| 2 | 2 | Me | OH | OH | NHMe | NHMe |
| 2 | 2 | Me | OH | OH | NHEt | NHEt |
| 2 | 2 | Me | OH | OH | NHPr | NHPr |
| 2 | 2 | Me | OH | OH | NHAc | NHAc |
| 2 | 2 | Me | OH | OH | CHO | CHO |
| 2 | 2 | Et | OH | OH | Br | Br |
| 2 | 2 | Et | OH | OH | Cl | Cl |
| 2 | 2 | Et | OH | OH | I | I |
| 2 | 2 | Et | OH | OH | Ac | Ac |
| 2 | 2 | Et | OH | OH | SO₃H | SO₃H |
| 2 | 2 | Et | OH | OH | Me | Me |
| 2 | 2 | Et | OH | OH | Et | Et |
| 2 | 2 | Et | OH | OH | Pr | Pr |
| 2 | 2 | Et | OH | OH | NO₂ | NO₂ |
| 2 | 2 | Et | OH | OH | CO₂H | CO₂H |
| 2 | 2 | Et | OH | OH | CO₂Me | CO₂Me |
| 2 | 2 | Et | OH | OH | CO₂Et | CO₂Et |
| 2 | 2 | Et | OH | OH | CO₂Pr | CO₂Pr |
| 2 | 2 | Et | OH | OH | CONH₂ | CONH₂ |
| 2 | 2 | Et | OH | OH | CN | CN |
| 2 | 2 | Et | OH | OH | OH | OH |
| 2 | 2 | Et | OH | OH | NH₂ | NH₂ |
| 2 | 2 | Et | OH | OH | NHMe | NHMe |
| 2 | 2 | Et | OH | OH | NHEt | NHEt |
| 2 | 2 | Et | OH | OH | NHPr | NHPr |
| 2 | 2 | Et | OH | OH | NHAc | NHAc |
| 2 | 2 | Et | OH | OH | CHO | CHO |
| 2 | 2 | Ac | OH | OH | Br | Br |
| 2 | 2 | Ac | OH | OH | Cl | Cl |
| 2 | 2 | Ac | OH | OH | I | I |
| 2 | 2 | Ac | OH | OH | Ac | Ac |
| 2 | 2 | Ac | OH | OH | SO₃H | SO₃H |
| 2 | 2 | Ac | OH | OH | Me | Me |
| 2 | 2 | Ac | OH | OH | Et | Et |
| 2 | 2 | Ac | OH | OH | Pr | Pr |
| 2 | 2 | Ac | OH | OH | NO₂ | NO₂ |
| 2 | 2 | Ac | OH | OH | CO₂H | CO₂H |
| 2 | 2 | Ac | OH | OH | CO₂Me | CO₂Me |
| 2 | 2 | Ac | OH | OH | CO₂Et | CO₂Et |
| 2 | 2 | Ac | OH | OH | CO₂Pr | CO₂Pr |
| 2 | 2 | Ac | OH | OH | CONH₂ | CONH₂ |
| 2 | 2 | Ac | OH | OH | CN | CN |
| 2 | 2 | Ac | OH | OH | OH | OH |
| 2 | 2 | Ac | OH | OH | NH₂ | NH₂ |
| 2 | 2 | Ac | OH | OH | NHMe | NHMe |
| 2 | 2 | Ac | OH | OH | NHEt | NHEt |
| 2 | 2 | Ac | OH | OH | NHPr | NHPr |
| 2 | 2 | Ac | OH | OH | NHAc | NHAc |
| 2 | 2 | Ac | OH | OH | CHO | CHO |

TABLE A

Formula I (n-oxide or free base)

| m | n | R | a,b | c,d | Y | Z |
|---|---|---|-----|-----|---|---|
| 0 | 0 | H | C(O) | C(O) | — | — |
| 0 | 0 | Me | C(O) | C(O) | — | — |
| 0 | 0 | Et | C(O) | C(O) | — | — |
| 0 | 0 | Ac | C(O) | C(O) | — | — |
| 1 | 0 | H | C(O) | C(O) | Br | — |
| 1 | 0 | H | C(O) | C(O) | Cl | — |
| 1 | 0 | H | C(O) | C(O) | I | — |
| 1 | 0 | H | C(O) | C(O) | Ac | — |
| 1 | 0 | H | C(O) | C(O) | SO₃H | — |
| 1 | 0 | H | C(O) | C(O) | Me | — |
| 1 | 0 | H | C(O) | C(O) | Et | — |
| 1 | 0 | H | C(O) | C(O) | Pr | — |
| 1 | 0 | H | C(O) | C(O) | NO₂ | — |
| 1 | 0 | H | C(O) | C(O) | CO₂H | — |
| 1 | 0 | H | C(O) | C(O) | CO₂Me | — |
| 1 | 0 | H | C(O) | C(O) | CO₂Et | — |
| 1 | 0 | H | C(O) | C(O) | CO₂Pr | — |
| 1 | 0 | H | C(O) | C(O) | CONH₂ | — |
| 1 | 0 | H | C(O) | C(O) | CN | — |
| 1 | 0 | H | C(O) | C(O) | OH | — |
| 1 | 0 | H | C(O) | C(O) | NH₂ | — |
| 1 | 0 | H | C(O) | C(O) | NHMe | — |
| 1 | 0 | H | C(O) | C(O) | NHEt | — |
| 1 | 0 | H | C(O) | C(O) | NHPr | — |
| 1 | 0 | H | C(O) | C(O) | NHAc | — |
| 1 | 0 | H | C(O) | C(O) | CHO | — |
| 1 | 0 | Me | C(O) | C(O) | Br | — |
| 1 | 0 | Me | C(O) | C(O) | Cl | — |
| 1 | 0 | Me | C(O) | C(O) | I | — |
| 1 | 0 | Me | C(O) | C(O) | Ac | — |
| 1 | 0 | Me | C(O) | C(O) | SO₃H | — |
| 1 | 0 | Me | C(O) | C(O) | Me | — |
| 1 | 0 | Me | C(O) | C(O) | Et | — |
| 1 | 0 | Me | C(O) | C(O) | Pr | — |
| 1 | 0 | Me | C(O) | C(O) | NO₂ | — |
| 1 | 0 | Me | C(O) | C(O) | CO₂H | — |
| 1 | 0 | Me | C(O) | C(O) | CO₂Me | — |
| 1 | 0 | Me | C(O) | C(O) | CO₂Et | — |
| 1 | 0 | Me | C(O) | C(O) | CO₂Pr | — |

TABLE A-continued

Formula I (n-oxide or free base)

| m | n | R | a,b | c,d | Y | Z |
|---|---|---|---|---|---|---|
| 1 | 0 | Me | C(O) | C(O) | $CONH_2$ | — |
| 1 | 0 | Me | C(O) | C(O) | CN | — |
| 1 | 0 | Me | C(O) | C(O) | OH | — |
| 1 | 0 | Me | C(O) | C(O) | $NH_2$ | — |
| 1 | 0 | Me | C(O) | C(O) | NHMe | — |
| 1 | 0 | Me | C(O) | C(O) | NHEt | — |
| 1 | 0 | Me | C(O) | C(O) | NHPr | — |
| 1 | 0 | Me | C(O) | C(O) | NHAc | — |
| 1 | 0 | Me | C(O) | C(O) | CHO | — |
| 1 | 0 | Et | C(O) | C(O) | Br | — |
| 1 | 0 | Et | C(O) | C(O) | Cl | — |
| 1 | 0 | Et | C(O) | C(O) | I | — |
| 1 | 0 | Et | C(O) | C(O) | Ac | — |
| 1 | 0 | Et | C(O) | C(O) | $SO_3H$ | — |
| 1 | 0 | Et | C(O) | C(O) | Me | — |
| 1 | 0 | Et | C(O) | C(O) | Et | — |
| 1 | 0 | Et | C(O) | C(O) | Pr | — |
| 1 | 0 | Et | C(O) | C(O) | $NO_2$ | — |
| 1 | 0 | Et | C(O) | C(O) | $CO_2H$ | — |
| 1 | 0 | Et | C(O) | C(O) | $CO_2Me$ | — |
| 1 | 0 | Et | C(O) | C(O) | $CO_2Et$ | — |
| 1 | 0 | Et | C(O) | C(O) | $CO_2Pr$ | — |
| 1 | 0 | Et | C(O) | C(O) | $CONH_2$ | — |
| 1 | 0 | Et | C(O) | C(O) | CN | — |
| 1 | 0 | Et | C(O) | C(O) | OH | — |
| 1 | 0 | Et | C(O) | C(O) | $NH_2$ | — |
| 1 | 0 | Et | C(O) | C(O) | NHMe | — |
| 1 | 0 | Et | C(O) | C(O) | NHEt | — |
| 1 | 0 | Et | C(O) | C(O) | NHPr | — |
| 1 | 0 | Et | C(O) | C(O) | NHAc | — |
| 1 | 0 | Et | C(O) | C(O) | CHO | — |
| 1 | 0 | Ac | C(O) | C(O) | Br | — |
| 1 | 0 | Ac | C(O) | C(O) | Cl | — |
| 1 | 0 | Ac | C(O) | C(O) | I | — |
| 1 | 0 | Ac | C(O) | C(O) | Ac | — |
| 1 | 0 | Ac | C(O) | C(O) | $SO_3H$ | — |
| 1 | 0 | Ac | C(O) | C(O) | Me | — |
| 1 | 0 | Ac | C(O) | C(O) | Et | — |
| 1 | 0 | Ac | C(O) | C(O) | Pr | — |
| 1 | 0 | Ac | C(O) | C(O) | $NO_2$ | — |
| 1 | 0 | Ac | C(O) | C(O) | $CO_2H$ | — |
| 1 | 0 | Ac | C(O) | C(O) | $CO_2Me$ | — |
| 1 | 0 | Ac | C(O) | C(O) | $CO_2Et$ | — |
| 1 | 0 | Ac | C(O) | C(O) | $CO_2Pr$ | — |
| 1 | 0 | Ac | C(O) | C(O) | $CONH_2$ | — |
| 1 | 0 | Ac | C(O) | C(O) | CN | — |
| 1 | 0 | Ac | C(O) | C(O) | OH | — |
| 1 | 0 | Ac | C(O) | C(O) | $NH_2$ | — |
| 1 | 0 | Ac | C(O) | C(O) | NHMe | — |
| 1 | 0 | Ac | C(O) | C(O) | NHEt | — |
| 1 | 0 | Ac | C(O) | C(O) | NHPr | — |
| 1 | 0 | Ac | C(O) | C(O) | NHAc | — |
| 1 | 0 | Ac | C(O) | C(O) | CHO | — |
| 0 | 1 | H | C(O) | C(O) | — | Br |
| 0 | 1 | H | C(O) | C(O) | — | Cl |
| 0 | 1 | H | C(O) | C(O) | — | I |
| 0 | 1 | H | C(O) | C(O) | — | Ac |
| 0 | 1 | H | C(O) | C(O) | — | $SO_3H$ |
| 0 | 1 | H | C(O) | C(O) | — | Me |
| 0 | 1 | H | C(O) | C(O) | — | Et |
| 0 | 1 | H | C(O) | C(O) | — | Pr |
| 0 | 1 | H | C(O) | C(O) | — | $NO_2$ |
| 0 | 1 | H | C(O) | C(O) | — | $CO_2H$ |
| 0 | 1 | H | C(O) | C(O) | — | $CO_2Me$ |
| 0 | 1 | H | C(O) | C(O) | — | $CO_2Et$ |
| 0 | 1 | H | C(O) | C(O) | — | $CO_2Pr$ |
| 0 | 1 | H | C(O) | C(O) | — | $CONH_2$ |
| 0 | 1 | H | C(O) | C(O) | — | CN |
| 0 | 1 | H | C(O) | C(O) | — | OH |
| 0 | 1 | H | C(O) | C(O) | — | $NH_2$ |
| 0 | 1 | H | C(O) | C(O) | — | NHMe |
| 0 | 1 | H | C(O) | C(O) | — | NHEt |
| 0 | 1 | H | C(O) | C(O) | — | NHPr |
| 0 | 1 | H | C(O) | C(O) | — | NHAc |
| 0 | 1 | H | C(O) | C(O) | — | CHO |
| 0 | 1 | Me | C(O) | C(O) | — | Br |
| 0 | 1 | Me | C(O) | C(O) | — | Cl |
| 0 | 1 | Me | C(O) | C(O) | — | I |
| 0 | 1 | Me | C(O) | C(O) | — | Ac |
| 0 | 1 | Me | C(O) | C(O) | — | $SO_3H$ |
| 0 | 1 | Me | C(O) | C(O) | — | Me |
| 0 | 1 | Me | C(O) | C(O) | — | Et |
| 0 | 1 | Me | C(O) | C(O) | — | Pr |
| 0 | 1 | Me | C(O) | C(O) | — | $NO_2$ |
| 0 | 1 | Me | C(O) | C(O) | — | $CO_2H$ |
| 0 | 1 | Me | C(O) | C(O) | — | $CO_2Me$ |
| 0 | 1 | Me | C(O) | C(O) | — | $CO_2Et$ |
| 0 | 1 | Me | C(O) | C(O) | — | $CO_2Pr$ |
| 0 | 1 | Me | C(O) | C(O) | — | $CONH_2$ |
| 0 | 1 | Me | C(O) | C(O) | — | CN |
| 0 | 1 | Me | C(O) | C(O) | — | OH |
| 0 | 1 | Me | C(O) | C(O) | — | $NH_2$ |
| 0 | 1 | Me | C(O) | C(O) | — | NHMe |
| 0 | 1 | Me | C(O) | C(O) | — | NHEt |
| 0 | 1 | Me | C(O) | C(O) | — | NHPr |
| 0 | 1 | Me | C(O) | C(O) | — | NHAc |
| 0 | 1 | Me | C(O) | C(O) | — | CHO |
| 0 | 1 | Et | C(O) | C(O) | — | Br |
| 0 | 1 | Et | C(O) | C(O) | — | Cl |
| 0 | 1 | Et | C(O) | C(O) | — | I |
| 0 | 1 | Et | C(O) | C(O) | — | Ac |
| 0 | 1 | Et | C(O) | C(O) | — | $SO_3H$ |
| 0 | 1 | Et | C(O) | C(O) | — | Me |
| 0 | 1 | Et | C(O) | C(O) | — | Et |
| 0 | 1 | Et | C(O) | C(O) | — | Pr |
| 0 | 1 | Et | C(O) | C(O) | — | $NO_2$ |
| 0 | 1 | Et | C(O) | C(O) | — | $CO_2H$ |
| 0 | 1 | Et | C(O) | C(O) | — | $CO_2Me$ |
| 0 | 1 | Et | C(O) | C(O) | — | $CO_2Et$ |
| 0 | 1 | Et | C(O) | C(O) | — | $CO_2Pr$ |
| 0 | 1 | Et | C(O) | C(O) | — | $CONH_2$ |
| 0 | 1 | Et | C(O) | C(O) | — | CN |
| 0 | 1 | Et | C(O) | C(O) | — | OH |
| 0 | 1 | Et | C(O) | C(O) | — | $NH_2$ |
| 0 | 1 | Et | C(O) | C(O) | — | NHMe |
| 0 | 1 | Et | C(O) | C(O) | — | NHEt |
| 0 | 1 | Et | C(O) | C(O) | — | NHPr |
| 0 | 1 | Et | C(O) | C(O) | — | NHAc |
| 0 | 1 | Et | C(O) | C(O) | — | CHO |
| 0 | 1 | Ac | C(O) | C(O) | — | Br |
| 0 | 1 | Ac | C(O) | C(O) | — | Cl |
| 0 | 1 | Ac | C(O) | C(O) | — | I |
| 0 | 1 | Ac | C(O) | C(O) | — | Ac |
| 0 | 1 | Ac | C(O) | C(O) | — | $SO_3H$ |
| 0 | 1 | Ac | C(O) | C(O) | — | Me |
| 0 | 1 | Ac | C(O) | C(O) | — | Et |
| 0 | 1 | Ac | C(O) | C(O) | — | Pr |
| 0 | 1 | Ac | C(O) | C(O) | — | $NO_2$ |
| 0 | 1 | Ac | C(O) | C(O) | — | $CO_2H$ |
| 0 | 1 | Ac | C(O) | C(O) | — | $CO_2Me$ |
| 0 | 1 | Ac | C(O) | C(O) | — | $CO_2Et$ |
| 0 | 1 | Ac | C(O) | C(O) | — | $CO_2Pr$ |
| 0 | 1 | Ac | C(O) | C(O) | — | $CONH_2$ |
| 0 | 1 | Ac | C(O) | C(O) | — | CN |
| 0 | 1 | Ac | C(O) | C(O) | — | OH |
| 0 | 1 | Ac | C(O) | C(O) | — | $NH_2$ |
| 0 | 1 | Ac | C(O) | C(O) | — | NHMe |
| 0 | 1 | Ac | C(O) | C(O) | — | NHEt |
| 0 | 1 | Ac | C(O) | C(O) | — | NHPr |
| 0 | 1 | Ac | C(O) | C(O) | — | NHAc |
| 0 | 1 | Ac | C(O) | C(O) | — | CHO |
| 1 | 1 | H | C(O) | C(O) | Br | Br |
| 1 | 1 | H | C(O) | C(O) | Cl | Cl |
| 1 | 1 | H | C(O) | C(O) | I | I |
| 1 | 1 | H | C(O) | C(O) | Ac | Ac |
| 1 | 1 | H | C(O) | C(O) | $SO_3H$ | $SO_3H$ |
| 1 | 1 | H | C(O) | C(O) | Me | Me |
| 1 | 1 | H | C(O) | C(O) | Et | Et |
| 1 | 1 | H | C(O) | C(O) | Pr | Pr |
| 1 | 1 | H | C(O) | C(O) | $NO_2$ | $NO_2$ |

TABLE A-continued

Formula I (n-oxide or free base)

| m | n | R | a,b | c,d | Y | Z |
|---|---|---|---|---|---|---|
| 1 | 1 | H | C(O) | C(O) | $CO_2H$ | $CO_2H$ |
| 1 | 1 | H | C(O) | C(O) | $CO_2Me$ | $CO_2Me$ |
| 1 | 1 | H | C(O) | C(O) | $CO_2Et$ | $CO_2Et$ |
| 1 | 1 | H | C(O) | C(O) | $CO_2Pr$ | $CO_2Pr$ |
| 1 | 1 | H | C(O) | C(O) | $CONH_2$ | $CONH_2$ |
| 1 | 1 | H | C(O) | C(O) | CN | CN |
| 1 | 1 | H | C(O) | C(O) | OH | OH |
| 1 | 1 | H | C(O) | C(O) | $NH_2$ | $NH_2$ |
| 1 | 1 | H | C(O) | C(O) | NHMe | NHMe |
| 1 | 1 | H | C(O) | C(O) | NHEt | NHEt |
| 1 | 1 | H | C(O) | C(O) | NHPr | NHPr |
| 1 | 1 | H | C(O) | C(O) | NHAc | NHAc |
| 1 | 1 | H | C(O) | C(O) | CHO | CHO |
| 1 | 1 | Me | C(O) | C(O) | Br | Br |
| 1 | 1 | Me | C(O) | C(O) | Cl | Cl |
| 1 | 1 | Me | C(O) | C(O) | I | I |
| 1 | 1 | Me | C(O) | C(O) | Ac | Ac |
| 1 | 1 | Me | C(O) | C(O) | $SO_3H$ | $SO_3H$ |
| 1 | 1 | Me | C(O) | C(O) | Me | Me |
| 1 | 1 | Me | C(O) | C(O) | Et | Et |
| 1 | 1 | Me | C(O) | C(O) | Pr | Pr |
| 1 | 1 | Me | C(O) | C(O) | $NO_2$ | $NO_2$ |
| 1 | 1 | Me | C(O) | C(O) | $CO_2H$ | $CO_2H$ |
| 1 | 1 | Me | C(O) | C(O) | $CO_2Me$ | $CO_2Me$ |
| 1 | 1 | Me | C(O) | C(O) | $CO_2Et$ | $CO_2Et$ |
| 1 | 1 | Me | C(O) | C(O) | $CO_2Pr$ | $CO_2Pr$ |
| 1 | 1 | Me | C(O) | C(O) | $CONH_2$ | $CONH_2$ |
| 1 | 1 | Me | C(O) | C(O) | CN | CN |
| 1 | 1 | Me | C(O) | C(O) | OH | OH |
| 1 | 1 | Me | C(O) | C(O) | $NH_2$ | $NH_2$ |
| 1 | 1 | Me | C(O) | C(O) | NHMe | NHMe |
| 1 | 1 | Me | C(O) | C(O) | NHEt | NHEt |
| 1 | 1 | Me | C(O) | C(O) | NHPr | NHPr |
| 1 | 1 | Me | C(O) | C(O) | NHAc | NHAc |
| 1 | 1 | Me | C(O) | C(O) | CHO | CHO |
| 1 | 1 | Et | C(O) | C(O) | Br | Br |
| 1 | 1 | Et | C(O) | C(O) | Cl | Cl |
| 1 | 1 | Et | C(O) | C(O) | I | I |
| 1 | 1 | Et | C(O) | C(O) | Ac | Ac |
| 1 | 1 | Et | C(O) | C(O) | $SO_3H$ | $SO_3H$ |
| 1 | 1 | Et | C(O) | C(O) | Me | Me |
| 1 | 1 | Et | C(O) | C(O) | Et | Et |
| 1 | 1 | Et | C(O) | C(O) | Pr | Pr |
| 1 | 1 | Et | C(O) | C(O) | $NO_2$ | $NO_2$ |
| 1 | 1 | Et | C(O) | C(O) | $CO_2H$ | $CO_2H$ |
| 1 | 1 | Et | C(O) | C(O) | $CO_2Me$ | $CO_2Me$ |
| 1 | 1 | Et | C(O) | C(O) | $CO_2Et$ | $CO_2Et$ |
| 1 | 1 | Et | C(O) | C(O) | $CO_2Pr$ | $CO_2Pr$ |
| 1 | 1 | Et | C(O) | C(O) | $CONH_2$ | $CONH_2$ |
| 1 | 1 | Et | C(O) | C(O) | CN | CN |
| 1 | 1 | Et | C(O) | C(O) | OH | OH |
| 1 | 1 | Et | C(O) | C(O) | $NH_2$ | $NH_2$ |
| 1 | 1 | Et | C(O) | C(O) | NHMe | NHMe |
| 1 | 1 | Et | C(O) | C(O) | NHEt | NHEt |
| 1 | 1 | Et | C(O) | C(O) | NHPr | NHPr |
| 1 | 1 | Et | C(O) | C(O) | NHAc | NHAc |
| 1 | 1 | Et | C(O) | C(O) | CHO | CHO |
| 1 | 1 | Ac | C(O) | C(O) | Br | Br |
| 1 | 1 | Ac | C(O) | C(O) | Cl | Cl |
| 1 | 1 | Ac | C(O) | C(O) | I | I |
| 1 | 1 | Ac | C(O) | C(O) | Ac | Ac |
| 1 | 1 | Ac | C(O) | C(O) | $SO_3H$ | $SO_3H$ |
| 1 | 1 | Ac | C(O) | C(O) | Me | Me |
| 1 | 1 | Ac | C(O) | C(O) | Et | Et |
| 1 | 1 | Ac | C(O) | C(O) | Pr | Pr |
| 1 | 1 | Ac | C(O) | C(O) | $NO_2$ | $NO_2$ |
| 1 | 1 | Ac | C(O) | C(O) | $CO_2H$ | $CO_2H$ |
| 1 | 1 | Ac | C(O) | C(O) | $CO_2Me$ | $CO_2Me$ |
| 1 | 1 | Ac | C(O) | C(O) | $CO_2Et$ | $CO_2Et$ |
| 1 | 1 | Ac | C(O) | C(O) | $CO_2Pr$ | $CO_2Pr$ |
| 1 | 1 | Ac | C(O) | C(O) | $CONH_2$ | $CONH_2$ |
| 1 | 1 | Ac | C(O) | C(O) | CN | CN |
| 1 | 1 | Ac | C(O) | C(O) | OH | OH |
| 1 | 1 | Ac | C(O) | C(O) | $NH_2$ | $NH_2$ |
| 1 | 1 | Ac | C(O) | C(O) | NHMe | NHMe |
| 1 | 1 | Ac | C(O) | C(O) | NHEt | NHEt |
| 1 | 1 | Ac | C(O) | C(O) | NHPr | NHPr |
| 1 | 1 | Ac | C(O) | C(O) | NHAc | NHAc |
| 1 | 1 | Ac | C(O) | C(O) | CHO | CHO |
| 2 | 1 | H | C(O) | C(O) | Br | Br |
| 2 | 1 | H | C(O) | C(O) | Cl | Cl |
| 2 | 1 | H | C(O) | C(O) | I | I |
| 2 | 1 | H | C(O) | C(O) | Ac | Ac |
| 2 | 1 | H | C(O) | C(O) | $SO_3H$ | $SO_3H$ |
| 2 | 1 | H | C(O) | C(O) | Me | Me |
| 2 | 1 | H | C(O) | C(O) | Et | Et |
| 2 | 1 | H | C(O) | C(O) | Pr | Pr |
| 2 | 1 | H | C(O) | C(O) | $NO_2$ | $NO_2$ |
| 2 | 1 | H | C(O) | C(O) | $CO_2H$ | $CO_2H$ |
| 2 | 1 | H | C(O) | C(O) | $CO_2Me$ | $CO_2Me$ |
| 2 | 1 | H | C(O) | C(O) | $CO_2Et$ | $CO_2Et$ |
| 2 | 1 | H | C(O) | C(O) | $CO_2Pr$ | $CO_2Pr$ |
| 2 | 1 | H | C(O) | C(O) | $CONH_2$ | $CONH_2$ |
| 2 | 1 | H | C(O) | C(O) | CN | CN |
| 2 | 1 | H | C(O) | C(O) | OH | OH |
| 2 | 1 | H | C(O) | C(O) | $NH_2$ | $NH_2$ |
| 2 | 1 | H | C(O) | C(O) | NHMe | NHMe |
| 2 | 1 | H | C(O) | C(O) | NHEt | NHEt |
| 2 | 1 | H | C(O) | C(O) | NHPr | NHPr |
| 2 | 1 | H | C(O) | C(O) | NHAc | NHAc |
| 2 | 1 | H | C(O) | C(O) | CHO | CHO |
| 2 | 1 | Me | C(O) | C(O) | Br | Br |
| 2 | 1 | Me | C(O) | C(O) | Cl | Cl |
| 2 | 1 | Me | C(O) | C(O) | I | I |
| 2 | 1 | Me | C(O) | C(O) | Ac | Ac |
| 2 | 1 | Me | C(O) | C(O) | $SO_3H$ | $SO_3H$ |
| 2 | 1 | Me | C(O) | C(O) | Me | Me |
| 2 | 1 | Me | C(O) | C(O) | Et | Et |
| 2 | 1 | Me | C(O) | C(O) | Pr | Pr |
| 2 | 1 | Me | C(O) | C(O) | $NO_2$ | $NO_2$ |
| 2 | 1 | Me | C(O) | C(O) | $CO_2H$ | $CO_2H$ |
| 2 | 1 | Me | C(O) | C(O) | $CO_2Me$ | $CO_2Me$ |
| 2 | 1 | Me | C(O) | C(O) | $CO_2Et$ | $CO_2Et$ |
| 2 | 1 | Me | C(O) | C(O) | $CO_2Pr$ | $CO_2Pr$ |
| 2 | 1 | Me | C(O) | C(O) | $CONH_2$ | $CONH_2$ |
| 2 | 1 | Me | C(O) | C(O) | CN | CN |
| 2 | 1 | Me | C(O) | C(O) | OH | OH |
| 2 | 1 | Me | C(O) | C(O) | $NH_2$ | $NH_2$ |
| 2 | 1 | Me | C(O) | C(O) | NHMe | NHMe |
| 2 | 1 | Me | C(O) | C(O) | NHEt | NHEt |
| 2 | 1 | Me | C(O) | C(O) | NHPr | NHPr |
| 2 | 1 | Me | C(O) | C(O) | NHAc | NHAc |
| 2 | 1 | Me | C(O) | C(O) | CHO | CHO |
| 2 | 1 | Et | C(O) | C(O) | Br | Br |
| 2 | 1 | Et | C(O) | C(O) | Cl | Cl |
| 2 | 1 | Et | C(O) | C(O) | I | I |
| 2 | 1 | Et | C(O) | C(O) | Ac | Ac |
| 2 | 1 | Et | C(O) | C(O) | $SO_3H$ | $SO_3H$ |
| 2 | 1 | Et | C(O) | C(O) | Me | Me |
| 2 | 1 | Et | C(O) | C(O) | Et | Et |
| 2 | 1 | Et | C(O) | C(O) | Pr | Pr |
| 2 | 1 | Et | C(O) | C(O) | $NO_2$ | $NO_2$ |
| 2 | 1 | Et | C(O) | C(O) | $CO_2H$ | $CO_2H$ |
| 2 | 1 | Et | C(O) | C(O) | $CO_2Me$ | $CO_2Me$ |
| 2 | 1 | Et | C(O) | C(O) | $CO_2Et$ | $CO_2Et$ |
| 2 | 1 | Et | C(O) | C(O) | $CO_2Pr$ | $CO_2Pr$ |
| 2 | 1 | Et | C(O) | C(O) | $CONH_2$ | $CONH_2$ |
| 2 | 1 | Et | C(O) | C(O) | CN | CN |
| 2 | 1 | Et | C(O) | C(O) | OH | OH |
| 2 | 1 | Et | C(O) | C(O) | $NH_2$ | $NH_2$ |
| 2 | 1 | Et | C(O) | C(O) | NHMe | NHMe |
| 2 | 1 | Et | C(O) | C(O) | NHEt | NHEt |
| 2 | 1 | Et | C(O) | C(O) | NHPr | NHPr |
| 2 | 1 | Et | C(O) | C(O) | NHAc | NHAc |
| 2 | 1 | Et | C(O) | C(O) | CHO | CHO |
| 2 | 1 | Ac | C(O) | C(O) | Br | Br |
| 2 | 1 | Ac | C(O) | C(O) | Cl | Cl |
| 2 | 1 | Ac | C(O) | C(O) | I | I |
| 2 | 1 | Ac | C(O) | C(O) | Ac | Ac |
| 2 | 1 | Ac | C(O) | C(O) | $SO_3H$ | $SO_3H$ |

TABLE A-continued

Formula I (n-oxide or free base)

| m | n | R | a,b | c,d | Y | Z |
|---|---|---|---|---|---|---|
| 2 | 1 | Ac | C(O) | C(O) | Me | Me |
| 2 | 1 | Ac | C(O) | C(O) | Et | Et |
| 2 | 1 | Ac | C(O) | C(O) | Pr | Pr |
| 2 | 1 | Ac | C(O) | C(O) | NO$_2$ | NO$_2$ |
| 2 | 1 | Ac | C(O) | C(O) | CO$_2$H | CO$_2$H |
| 2 | 1 | Ac | C(O) | C(O) | CO$_2$Me | CO$_2$Me |
| 2 | 1 | Ac | C(O) | C(O) | CO$_2$Et | CO$_2$Et |
| 2 | 1 | Ac | C(O) | C(O) | CO$_2$Pr | CO$_2$Pr |
| 2 | 1 | Ac | C(O) | C(O) | CONH$_2$ | CONH$_2$ |
| 2 | 1 | Ac | C(O) | C(O) | CN | CN |
| 2 | 1 | Ac | C(O) | C(O) | OH | OH |
| 2 | 1 | Ac | C(O) | C(O) | NH$_2$ | NH$_2$ |
| 2 | 1 | Ac | C(O) | C(O) | NHMe | NHMe |
| 2 | 1 | Ac | C(O) | C(O) | NHEt | NHEt |
| 2 | 1 | Ac | C(O) | C(O) | NHPr | NHPr |
| 2 | 1 | Ac | C(O) | C(O) | NHAc | NHAc |
| 2 | 1 | Ac | C(O) | C(O) | CHO | CHO |
| 1 | 2 | H | C(O) | C(O) | Br | Br |
| 1 | 2 | H | C(O) | C(O) | Cl | Cl |
| 1 | 2 | H | C(O) | C(O) | I | I |
| 1 | 2 | H | C(O) | C(O) | Ac | Ac |
| 1 | 2 | H | C(O) | C(O) | SO$_3$H | SO$_3$H |
| 1 | 2 | H | C(O) | C(O) | Me | Me |
| 1 | 2 | H | C(O) | C(O) | Et | Et |
| 1 | 2 | H | C(O) | C(O) | Pr | Pr |
| 1 | 2 | H | C(O) | C(O) | NO$_2$ | NO$_2$ |
| 1 | 2 | H | C(O) | C(O) | CO$_2$H | CO$_2$H |
| 1 | 2 | H | C(O) | C(O) | CO$_2$Me | CO$_2$Me |
| 1 | 2 | H | C(O) | C(O) | CO$_2$Et | CO$_2$Et |
| 1 | 2 | H | C(O) | C(O) | CO$_2$Pr | CO$_2$Pr |
| 1 | 2 | H | C(O) | C(O) | CONH$_2$ | CONH$_2$ |
| 1 | 2 | R | C(O) | C(O) | CN | CN |
| 1 | 2 | H | C(O) | C(O) | OH | OH |
| 1 | 2 | H | C(O) | C(O) | NH$_2$ | NH$_2$ |
| 1 | 2 | H | C(O) | C(O) | NHMe | NHMe |
| 1 | 2 | H | C(O) | C(O) | NHEt | NHEt |
| 1 | 2 | H | C(O) | C(O) | NHPr | NHPr |
| 1 | 2 | H | C(O) | C(O) | NHAc | NHAc |
| 1 | 2 | H | C(O) | C(O) | CHO | CHO |
| 1 | 2 | Me | C(O) | C(O) | Br | Br |
| 1 | 2 | Me | C(O) | C(O) | Cl | Cl |
| 1 | 2 | Me | C(O) | C(O) | I | I |
| 1 | 2 | Me | C(O) | C(O) | Ac | Ac |
| 1 | 2 | Me | C(O) | C(O) | SO$_3$H | SO$_3$H |
| 1 | 2 | Me | C(O) | C(O) | Me | Me |
| 1 | 2 | Me | C(O) | C(O) | Et | Et |
| 1 | 2 | Me | C(O) | C(O) | Pr | Pr |
| 1 | 2 | Me | C(O) | C(O) | NO$_2$ | NO$_2$ |
| 1 | 2 | Me | C(O) | C(O) | CO$_2$H | CO$_2$H |
| 1 | 2 | Me | C(O) | C(O) | CO$_2$Me | CO$_2$Me |
| 1 | 2 | Me | C(O) | C(O) | CO$_2$Et | CO$_2$Et |
| 1 | 2 | Me | C(O) | C(O) | CO$_2$Pr | CO$_2$Pr |
| 1 | 2 | Me | C(O) | C(O) | CONH$_2$ | CONH$_2$ |
| 1 | 2 | Me | C(O) | C(O) | CN | CN |
| 1 | 2 | Me | C(O) | C(O) | OH | OH |
| 1 | 2 | Me | C(O) | C(O) | NH$_2$ | NH$_2$ |
| 1 | 2 | Me | C(O) | C(O) | NHMe | NHMe |
| 1 | 2 | Me | C(O) | C(O) | NHEt | NHEt |
| 1 | 2 | Me | C(O) | C(O) | NHPr | NHPr |
| 1 | 2 | Me | C(O) | C(O) | NHAc | NHAc |
| 1 | 2 | Me | C(O) | C(O) | CHO | CHO |
| 1 | 2 | Et | C(O) | C(O) | Br | Br |
| 1 | 2 | Et | C(O) | C(O) | Cl | Cl |
| 1 | 2 | Et | C(O) | C(O) | I | I |
| 1 | 2 | Et | C(O) | C(O) | Ac | Ac |
| 1 | 2 | Et | C(O) | C(O) | SO$_3$H | SO$_3$H |
| 1 | 2 | Et | C(O) | C(O) | Me | Me |
| 1 | 2 | Et | C(O) | C(O) | Et | Et |
| 1 | 2 | Et | C(O) | C(O) | Pr | Pr |
| 1 | 2 | Et | C(O) | C(O) | NO$_2$ | NO$_2$ |
| 1 | 2 | Et | C(O) | C(O) | CO$_2$H | CO$_2$H |
| 1 | 2 | Et | C(O) | C(O) | CO$_2$Me | CO$_2$Me |
| 1 | 2 | Et | C(O) | C(O) | CO$_2$Et | CO$_2$Et |
| 1 | 2 | Et | C(O) | C(O) | CO$_2$Pr | CO$_2$Pr |
| 1 | 2 | Et | C(O) | C(O) | CONH$_2$ | CONH$_2$ |
| 1 | 2 | Et | C(O) | C(O) | CN | CN |
| 1 | 2 | Et | C(O) | C(O) | OH | OH |
| 1 | 2 | Et | C(O) | C(O) | NH$_2$ | NH$_2$ |
| 1 | 2 | Et | C(O) | C(O) | NHMe | NHMe |
| 1 | 2 | Et | C(O) | C(O) | NHEt | NHEt |
| 1 | 2 | Et | C(O) | C(O) | NHPr | NHPr |
| 1 | 2 | Et | C(O) | C(O) | NHAc | NHAc |
| 1 | 2 | Et | C(O) | C(O) | CHO | CHO |
| 1 | 2 | Ac | C(O) | C(O) | Br | Br |
| 1 | 2 | Ac | C(O) | C(O) | Cl | Cl |
| 1 | 2 | Ac | C(O) | C(O) | I | I |
| 1 | 2 | Ac | C(O) | C(O) | Ac | Ac |
| 1 | 2 | Ac | C(O) | C(O) | SO$_3$H | SO$_3$H |
| 1 | 2 | Ac | C(O) | C(O) | Me | Me |
| 1 | 2 | Ac | C(O) | C(O) | Et | Et |
| 1 | 2 | Ac | C(O) | C(O) | Pr | Pr |
| 1 | 2 | Ac | C(O) | C(O) | NO$_2$ | NO$_2$ |
| 1 | 2 | Ac | C(O) | C(O) | CO$_2$H | CO$_2$H |
| 1 | 2 | Ac | C(O) | C(O) | CO$_2$Me | CO$_2$Me |
| 1 | 2 | Ac | C(O) | C(O) | CO$_2$Et | CO$_2$Et |
| 1 | 2 | Ac | C(O) | C(O) | CO$_2$Pr | CO$_2$Pr |
| 1 | 2 | Ac | C(O) | C(O) | CONH$_2$ | CONH$_2$ |
| 1 | 2 | Ac | C(O) | C(O) | CN | CN |
| 1 | 2 | Ac | C(O) | C(O) | OH | OH |
| 1 | 2 | Ac | C(O) | C(O) | NH$_2$ | NH$_2$ |
| 1 | 2 | Ac | C(O) | C(O) | NHMe | NHMe |
| 1 | 2 | Ac | C(O) | C(O) | NHEt | NHEt |
| 1 | 2 | Ac | C(O) | C(O) | NHPr | NHPr |
| 1 | 2 | Ac | C(O) | C(O) | NHAc | NHAc |
| 1 | 2 | Ac | C(O) | C(O) | CHO | CHO |
| 2 | 2 | H | C(O) | C(O) | Br | Br |
| 2 | 2 | H | C(O) | C(O) | Cl | Cl |
| 2 | 2 | H | C(O) | C(O) | I | I |
| 2 | 2 | H | C(O) | C(O) | Ac | Ac |
| 2 | 2 | H | C(O) | C(O) | SO$_3$H | SO$_3$H |
| 2 | 2 | H | C(O) | C(O) | Me | Me |
| 2 | 2 | H | C(O) | C(O) | Et | Et |
| 2 | 2 | H | C(O) | C(O) | Pr | Pr |
| 2 | 2 | H | C(O) | C(O) | NO$_2$ | NO$_2$ |
| 2 | 2 | H | C(O) | C(O) | CO$_2$H | CO$_2$H |
| 2 | 2 | H | C(O) | C(O) | CO$_2$Me | CO$_2$Me |
| 2 | 2 | H | C(O) | C(O) | CO$_2$Et | CO$_2$Et |
| 2 | 2 | H | C(O) | C(O) | CO$_2$Pr | CO$_2$Pr |
| 2 | 2 | H | C(O) | C(O) | CONH$_2$ | CONH$_2$ |
| 2 | 2 | H | C(O) | C(O) | CN | CN |
| 2 | 2 | H | C(O) | C(O) | OH | OH |
| 2 | 2 | H | C(O) | C(O) | NH$_2$ | NH$_2$ |
| 2 | 2 | H | C(O) | C(O) | NHMe | NHMe |
| 2 | 2 | H | C(O) | C(O) | NHEt | NHEt |
| 2 | 2 | H | C(O) | C(O) | NHPr | NHPr |
| 2 | 2 | H | C(O) | C(O) | NHAc | NHAc |
| 2 | 2 | H | C(O) | C(O) | CHO | CHO |
| 2 | 2 | Me | C(O) | C(O) | Br | Br |
| 2 | 2 | Me | C(O) | C(O) | Cl | Cl |
| 2 | 2 | Me | C(O) | C(O) | I | I |
| 2 | 2 | Me | C(O) | C(O) | Ac | Ac |
| 2 | 2 | Me | C(O) | C(O) | SO$_3$H | SO$_3$H |
| 2 | 2 | Me | C(O) | C(O) | Me | Me |
| 2 | 2 | Me | C(O) | C(O) | Et | Et |
| 2 | 2 | Me | C(O) | C(O) | Pr | Pr |
| 2 | 2 | Me | C(O) | C(O) | NO$_2$ | NO$_2$ |
| 2 | 2 | Me | C(O) | C(O) | CO$_2$H | CO$_2$H |
| 2 | 2 | Me | C(O) | C(O) | CO$_2$Me | CO$_2$Me |
| 2 | 2 | Me | C(O) | C(O) | CO$_2$Et | CO$_2$Et |
| 2 | 2 | Me | C(O) | C(O) | CO$_2$Pr | CO$_2$Pr |
| 2 | 2 | Me | C(O) | C(O) | CONH$_2$ | CONH$_2$ |
| 2 | 2 | Me | C(O) | C(O) | CN | CN |
| 2 | 2 | Me | C(O) | C(O) | OH | OH |
| 2 | 2 | Me | C(O) | C(O) | NH$_2$ | NH$_2$ |
| 2 | 2 | Me | C(O) | C(O) | NHMe | NHMe |
| 2 | 2 | Me | C(O) | C(O) | NHEt | NHEt |
| 2 | 2 | Me | C(O) | C(O) | NHPr | NHPr |
| 2 | 2 | Me | C(O) | C(O) | NHAc | NHAc |
| 2 | 2 | Me | C(O) | C(O) | CHO | CHO |
| 2 | 2 | Et | C(O) | C(O) | Br | Br |

TABLE A-continued

Formula I (n-oxide or free base)

| m | n | R | a,b | c,d | Y | Z |
|---|---|---|---|---|---|---|
| 2 | 2 | Et | C(O) | C(O) | Cl | Cl |
| 2 | 2 | Et | C(O) | C(O) | I | I |
| 2 | 2 | Et | C(O) | C(O) | Ac | Ac |
| 2 | 2 | Et | C(O) | C(O) | $SO_3H$ | $SO_3H$ |
| 2 | 2 | Et | C(O) | C(O) | Me | Me |
| 2 | 2 | Et | C(O) | C(O) | Et | Et |
| 2 | 2 | Et | C(O) | C(O) | Pr | Pr |
| 2 | 2 | Et | C(O) | C(O) | $NO_2$ | $NO_2$ |
| 2 | 2 | Et | C(O) | C(O) | $CO_2H$ | $CO_2H$ |
| 2 | 2 | Et | C(O) | C(O) | $CO_2Me$ | $CO_2Me$ |
| 2 | 2 | Et | C(O) | C(O) | $CO_2Et$ | $CO_2Et$ |
| 2 | 2 | Et | C(O) | C(O) | $CO_2Pr$ | $CO_2Pr$ |
| 2 | 2 | Et | C(O) | C(O) | $CONH_2$ | $CONH_2$ |
| 2 | 2 | Et | C(O) | C(O) | CN | CN |
| 2 | 2 | Et | C(O) | C(O) | OH | OH |
| 2 | 2 | Et | C(O) | C(O) | $NH_2$ | $NH_2$ |
| 2 | 2 | Et | C(O) | C(O) | NHMe | NHMe |
| 2 | 2 | Et | C(O) | C(O) | NHEt | NHEt |
| 2 | 2 | Et | C(O) | C(O) | NHPr | NHPr |
| 2 | 2 | Et | C(O) | C(O) | NHAc | NHAc |
| 2 | 2 | Et | C(O) | C(O) | CHO | CHO |
| 2 | 2 | Ac | C(O) | C(O) | Br | Br |
| 2 | 2 | Ac | C(O) | C(O) | Cl | Cl |
| 2 | 2 | Ac | C(O) | C(O) | I | I |
| 2 | 2 | Ac | C(O) | C(O) | Ac | Ac |
| 2 | 2 | Ac | C(O) | C(O) | $SO_3H$ | $SO_3H$ |
| 2 | 2 | Ac | C(O) | C(O) | Me | Me |
| 2 | 2 | Ac | C(O) | C(O) | Et | Et |
| 2 | 2 | Ac | C(O) | C(O) | Pr | Pr |
| 2 | 2 | Ac | C(O) | C(O) | $NO_2$ | $NO_2$ |
| 2 | 2 | Ac | C(O) | C(O) | $CO_2H$ | $CO_2H$ |
| 2 | 2 | Ac | C(O) | C(O) | $CO_2Me$ | $CO_2Me$ |
| 2 | 2 | Ac | C(O) | C(O) | $CO_2Et$ | $CO_2Et$ |
| 2 | 2 | Ac | C(O) | C(O) | $CO_2Pr$ | $CO_2Pr$ |
| 2 | 2 | Ac | C(O) | C(O) | $CONH_2$ | $CONH_2$ |
| 2 | 2 | Ac | C(O) | C(O) | CN | CN |
| 2 | 2 | Ac | C(O) | C(O) | OH | OH |
| 2 | 2 | Ac | C(O) | C(O) | $NH_2$ | $NH_2$ |
| 2 | 2 | Ac | C(O) | C(O) | NHMe | NHMe |
| 2 | 2 | Ac | C(O) | C(O) | NHEt | NHEt |
| 2 | 2 | Ac | C(O) | C(O) | NHPr | NHPr |
| 2 | 2 | Ac | C(O) | C(O) | NHAc | NHAc |
| 2 | 2 | Ac | C(O) | C(O) | CHO | CHO |

MICROORGANISM DEPOSIT

The Calothrix strain CAN 95/2 was depositied with the Australian Government Analytical Labortories (AGAL) at 1 Suakin Street, Pymble, N.S.W. 2073, Australia on May 21, 1999 and was assigned AGAL Accession No. NM99/03484.

What is claimed is:

1. A compound of Formula (I):

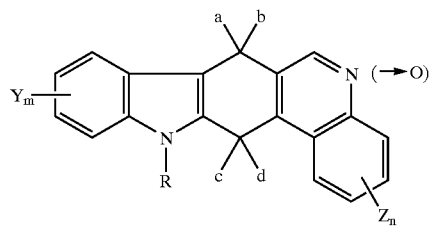

wherein
R is selected from hydrogen, alkyl, acyl, carboxyalkyl, carboalkoxyalkyl;
m and n are independently selected from 0, 1, 2;
each Y and each Z are independently selected from halo, acyl, nitro, amino, alkylamino, acylamino, hydroxy, acyloxy, alkoxy, alkyl, $CO_2H$, $CO_2$alkyl, $CONX_2$ (where each X is independently, H or alkyl), $SO_3H$, $SO_2NX_2$ (wherein each X is independently H or alkyl), nitrile, formyl, carboxyalkyl, carboalkoxyalkyl;
a, b, c and d are independently selected from hydrogen, hydroxy, alkoxy, acyloxy, alkyl; or,
a and b together and/or c and d together independently form a carbonyl group (C=O), an imine group (C=N—$R^1$, where $R^1$ is alkyl, hydroxy, alkoxy or amino $NR^2R^3$), or an alkene group (C=$CR^2R^3$, where $R^2$ and $R^3$ are independently hydrogen or alkyl) wherein the Compound of Formula (I) is as the N-oxide or unoxidized base,
or salt, derivative or prodrug thereof.

2. A compound of Formula (II):

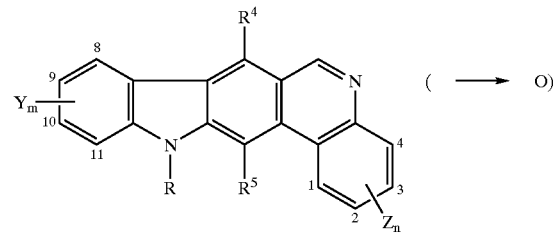

wherein
R is selected from hydrogen, alkyl, acyl carboxyalkyl, carboalkoxyalkyl;
in and n are independently selected from 0, 1, 2;
each Y and each Z are independently selected from halo, acyl, nitro, amino, alkylamino, acylamino, hydroxy, acyloxy, alkoxy, alkyl, $CO_2H$, $CO_2$alkyl, $CONX_2$ (wherein each X is independently selected from hydrogen or alkyl), sulfate, nitrile formyl carboxyalkyl, carboalkoxyalkyl; and
$R^4$ and $R^5$ are independently selected from hydrogen, hydroxy, alkoxy, acyloxy or alkyl, wherein the compound of Formula (II) is as the N-oxide or unoxidized base
or a salt, derivative or prodrug thereof.

3. A compound according to claim 1 or 2 wherein R is selected from the group consisting of hydrogen, methyl, ethyl or acetyl.

4. A compound according to claim 1 or 2 wherein m is 0 or 1.

5. A compound according to claim 1 or 2 wherein n is 0 or 1.

6. A compound according to claim 1 wherein at least one of a and b or c and d together form a carbonyl group, an imine group or an alkene group.

7. A compound according to claim 6 wherein one or both of a and b and c and d together form a carbonyl group.

8. A compound according to claim 1 or 2 wherein Y is selected from the group consisting of Cl, Br, I, OH, C(O)Me, C(O)Et, C(O)Pr, $NH_2$, NHMe, NHEt, NHPr, NHC(O)Me, OMe, OEt, OPr, $CO_2H$, $CO_2Me$, $CO_2Et$, $CO_2Pr$, $CONH_2$, $SO_3H$, $SO_2NH_2$, CHO, $OC(O)CH_3$.

9. A compound according to claim 1 or 2 wherein Z is selected from the group consisting of Cl, Br, I, OH, C(O)Me, C(O)Et, C(O)Pr, $NH_2$, NHMe, NHEt, NHPr, NHC(O)Me, OMe, OEt, OPr, $CO_2H$, $CO_2Me$, $CO_2Et$, $CO_2Pr$, $CONH_2$, $SO_3H$, $SO_2NH_2$, CHO, $OC(O)CH_3$.

10. A compound according to claim 1 wherein said compound is

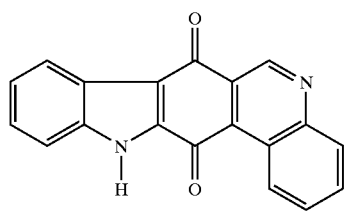

or its N-oxide.

11. A compound according to claim 2 wherein $R^4$ and $R^5$ are independently selected from hydroxy, alkoxy such as methoxy, ethoxy, propoxy, butyoxy, or acyloxy, such as acetoxy.

12. A compound according to claim 11 wherein $R^4$ and $R^5$ are both hydroxy.

13. A composition comprising a compound according to claim 1 or 2 together with a pharmaceutically acceptable carrier, diluent or excipient.

14. A method for the prophylaxis or treatment of malarial diseases in a mammal in need thereof comprising the administration of a prophylactic or treatment effective amount of a compound according to claim 1 or claim 2 to said mammal.

* * * * *

UNITED STATES PATENT AND TRADEMARK OFFICE
CERTIFICATE OF CORRECTION

PATENT NO. : 6,632,822 B1
DATED : October 14, 2003
INVENTOR(S) : Rickards et al.

It is certified that error appears in the above-identified patent and that said Letters Patent is hereby corrected as shown below:

Column 1,
Line 26, replace "humanp" with -- human, --.

Column 10,
Line 20, replace "zein" with -- zein, --.

Column 14,
Line 45, replace "$L^{-1}$" with -- $\mu L^{-1}$ --.

Column 15,
Line 1, replace "strain i" with -- strain --.

Column 27,
Line 32, replace "R" with -- H --.

Column 30,
Line 32, replace "in" with -- m --.

Signed and Sealed this

Sixth Day of July, 2004

JON W. DUDAS
*Acting Director of the United States Patent and Trademark Office*